(12) United States Patent
Scherkowski

(10) Patent No.: US 9,808,286 B2
(45) Date of Patent: Nov. 7, 2017

(54) DEVICE FOR THE REPEATED PIERCING OF AN ORGANIC TISSUE, AN APPLICATION MODULE AND A METHOD THEREOF

(71) Applicant: Technische Universitat Berlin, Berlin (DE)

(72) Inventor: Dirk Scherkowski, Berlin (DE)

(73) Assignee: Technische Universitaet Berlin, Berlin (DE)

( * ) Notice: Subject to any disclaimer, the term of this patent is extended or adjusted under 35 U.S.C. 154(b) by 77 days.

(21) Appl. No.: 13/739,086

(22) Filed: Jan. 11, 2013

(65) Prior Publication Data
US 2013/0184733 A1    Jul. 18, 2013

(30) Foreign Application Priority Data
Jan. 13, 2012  (DE) .................. 10 2012 100 308

(51) Int. Cl.
*A61B 17/34*    (2006.01)
*A61M 37/00*    (2006.01)
*A61B 17/20*    (2006.01)

(52) U.S. Cl.
CPC ........ *A61B 17/3476* (2013.01); *A61B 17/205* (2013.01); *A61M 37/00* (2013.01); *A61M 37/0084* (2013.01)

(58) Field of Classification Search
CPC ... A61B 17/205; A61B 17/3476; A61B 17/34; A61B 17/28; A61B 17/2804; A61B 17/2812; A61B 17/282; A61B 17/285; A61B 17/08; A61B 17/083; A61B 2017/3411; A61B 2017/2927; A61B 2017/2932; A61B 2017/2938; (Continued)

(56) References Cited

U.S. PATENT DOCUMENTS 3,010,455 A    11/1961  Cooper
6,123,678 A *   9/2000  Palmer et al. ................ 600/567
(Continued)

FOREIGN PATENT DOCUMENTS

CN    201658748 U    4/2010
EP    2 011 539 A1   1/2009
(Continued)

*Primary Examiner* — Darwin Erezo
*Assistant Examiner* — Katherine Schwiker
(74) *Attorney, Agent, or Firm* — Dinsmore & Shohl LLP

(57) ABSTRACT

A device for repeated piercing of an organic tissue and method thereof are disclosed. The device may comprise an arrangement of application tools each of which is connected to an operating mechanism and has a distal tool end which is formed for at least one application tool with a penetration device, whereby by way of the operating mechanism the tools can be displaced relative to each other between an initial position and a penetration position. During the relative movement, the effect direction of an application force provided by at least one application tool is counter to the effect direction of the application force provided by the other application tool. A mechanical actuation device, which is connected to the operating mechanism, is suitable for repeatedly effecting the relative displacement of the at least one application tool between the initial position and the penetration with an operating frequency.

17 Claims, 16 Drawing Sheets

(58) Field of Classification Search
CPC ........ A61B 2017/081; A61B 5/150977; A61B 5/150984; A61B 5/150412; A61B 5/15146; A61B 2018/143; A61M 37/00; A61M 37/0084; A61M 37/0076; A61M 37/0092; A61M 37/0015; A61M 5/3295; A61M 5/3297; A61M 5/3298; A61M 2037/0061; A61M 2037/0023; A61M 35/00; A61M 35/003; A01K 11/005
USPC ................ 606/185, 186, 205–207, 215, 216; 81/9.22
See application file for complete search history.

(56) References Cited

U.S. PATENT DOCUMENTS

| | | | |
|---|---|---|---|
| 6,506,210 B1* | 1/2003 | Kanner | A61B 17/0057 227/179.1 |
| 6,743,211 B1* | 6/2004 | Prausnitz | A61B 5/1411 424/449 |
| 7,828,811 B2* | 11/2010 | Kortenbach et al. | 606/142 |
| 2004/0116953 A1* | 6/2004 | Dixon | A61M 37/0076 606/186 |
| 2005/0187547 A1* | 8/2005 | Sugi | 606/48 |
| 2005/0209566 A1 | 9/2005 | Yeshurun et al. | |
| 2005/0274768 A1* | 12/2005 | Cummins | A61B 17/0057 227/175.1 |
| 2006/0265035 A1* | 11/2006 | Yachi et al. | 607/101 |
| 2008/0167680 A1* | 7/2008 | Voegele et al. | 606/206 |
| 2008/0294064 A1* | 11/2008 | Calasso et al. | 600/547 |
| 2009/0057369 A1* | 3/2009 | Smith | A61B 17/07207 227/175.1 |
| 2009/0125050 A1 | 5/2009 | Dixon | |
| 2009/0138029 A1* | 5/2009 | Saliman et al. | 606/144 |
| 2009/0143789 A1* | 6/2009 | Houser | A61B 17/0057 606/142 |
| 2010/0181364 A1* | 7/2010 | Shelton, IV | A61B 17/00491 227/180.1 |
| 2011/0245776 A1 | 10/2011 | Kendall | |

FOREIGN PATENT DOCUMENTS

| | | |
|---|---|---|
| EP | 2011539 A1 | 1/2009 |
| JP | 2000342332 A | 12/2000 |
| WO | 2008010573 A1 | 1/2008 |
| WO | WO 2009097621 A1 * | 8/2009 |

* cited by examiner

DEVICE FOR THE REPEATED PIERCING OF AN ORGANIC TISSUE, AN APPLICATION MODULE AND A METHOD THEREOF

TECHNICAL FIELD

The present disclosure relates to a device for the repeated piercing of an organic tissue, an application module for a device for the repeated piercing of an organic tissue, and a method thereof.

BACKGROUND

Organic tissues can come in various forms. More particularly, the human or animal skin is an organic tissue which constitutes an effective barrier against the penetration of high-molecular substances or microorganisms into the human body. Nevertheless, in order to be able to introduce therapeutically active agents or other substances, cosmetic substances, or, as in the case of tattooing or permanent make-up, dyes, coloring agents or pigments into the body via the skin, the skin, more particularly the outer layer of the skin, the epidermis, is made permeable to the relevant substances or pigments by way of holes or slits (piercing) produced by suitable cutting or piercing tools (penetrating tools) acting on the skin (cf., for example EP 2 011539 B1, US 2009/0125 050 A1).

From document JP 2000 342 332 A, a tattooing device is known in which a bundle of needles that are soldered together at one end is provided for penetrating the skin. In operation, the needles are moved back and forth as bundle. The piercing tips of the needles in the bundle can be bent away from each other.

The document US 2005/0209566 A1 discloses a device for applying an active substance on a biological material. In operation, the piercing tool performs a forward and return movement, which is superimposed by a pivoting movement.

Piercing and/or cutting open skin is also used without the accompanying application of an active substance for medical or cosmetic purposes. Here, cutting or piercing tools are usually used which for repeated penetration of the skin are coupled to a mechanical actuator which drives the penetrating tools with an operating frequency.

SUMMARY

A device for the repeated piercing of an organic tissue, as well as a method for the repeated piercing of an organic tissue, which are simple to use and allow careful and as painless as possible penetration of the organic tissue, more particularly animal or human skin, are disclosed.

The embodiments disclosed herein allow flexible and gentle penetration of an organic tissue, more particularly animal or human skin, whereby the penetration involves the insertion of the penetrating device into the organic tissue.

The arrangement of application tools in the device, each of which is held on the operating mechanism, can be moved between an initial position and a penetrating position. At the distal end of the tools, one or more of the application tools is/are provided with a penetration device. In the simplest case, the transition between the initial position and the penetrating position, i.e. the position in which the arrangement of application tools corresponds with the state in which the organic tissue is penetrated in operation, takes place in that only one of the application tools is moved in its position relative to the remaining application tools. For this, it is possible that either the one application tool or the remaining application tools is/are moved with the aid of the actuating mechanism. This results in a transition from the initial position of the arrangement of applications tools into the penetrating position of the arrangement. At the same time, the individual application tools can each be assigned an initial position and a penetrating position, more particularly in relation to the one or more moved application tools. In operation, the penetrating position means that the distal application end of at least one of the application tools of the arrangement provided with a penetration device has penetrated into the organic tissue.

In addition, a mechanical actuating device is provided which is connected to the operating mechanism and is suitable for repeatedly bringing about the relative movement of the at least one application tool between the initial position and the penetrating position with an operating frequency. The operating frequency of the repeated actuating movement generated by the actuating device can be about 5 Hz to about 200 Hz. Preferably, there is an operating frequency of about 20 Hz to about 200 Hz.

The device may be modularly structured. For example, the penetrating device can be arranged in an application module (piercing module), which in turn is detachably connected to an actuating module which holds the actuating device. A grip can be provided on the actuating model, which is held by the user with his/her fingers or hand when in operation. The actuating module can also form a handpiece. If a dispensing device is provided, this can be arranged on the application module or on the actuating module.

The application module may be provided with a coupling mechanism, which may be provided on rear end of the module. The coupling mechanism may be configured to couple to the actuating module. Such coupling may provide for coupling the actuating force provided by the actuating device into an actuating plunger while the application module and the actuating device are coupled together, e.g., by means of a screw and/or a plug-in connection.

When using the device it may be placed on the organic tissue in an area in which by means of penetration one or more openings in the tissue are to be produced. When using the device, on penetration into the organic tissue, an opening is produced which, for example, may be used for introducing one or more active substances or agents into the organic tissue. The penetration of the tissue may used for skin stimulation without substance application.

During the use of the device for applying active substances (application device), the removal of one or more active substances from a dispensing device and onto the organic tissue before, after and/or during penetration can be envisaged, whereby introduction into the organic tissue takes place during and/or after the penetration.

The applicable active substances which can be introduced via a tissue opening, for example a skin opening, into the tissue can include dyes, ink, coloring agents or pigments in connection with producing a tattoo or applying permanent make-up, cosmetic agents and medicinal active substances, for example for vaccination. Fluid substances that can be applied using the device include, for example, solutions, emulsions, colloidal solutions, dispersions, suspensions, lotions, creams, gels, substance in solid or particle form, such as, for example, pigments, particles, microparticles, nanoparticles, microcapsules or biological substances, such as, for example, proteins, peptides, enzymes, nucleic acids, genes, vectors, cells, hair follicles (dead), viruses, bacteria but also substances such as vesicles, micelles or nanorobots.

The device may be used for the various aforementioned applications.

The device for the repeated piercing of an organic tissue may be designed as a hand-held device.

The device or the individual modular elements thereof, for example the application or piercing module coupled to the actuating device, can be designed as disposable articles.

The dispensing device, which is configured to provide a substance to be applied and to supply it when using the device for tissue penetration, can, for example, be designed with a supply container which is in fluid connection with a supply opening, via which the substances can be dispensed. Dispensing devices of this type are known as such in various embodiments, for example in connection with devices for applying tattoos or permanent make-up. Here, it can be envisaged that the dispensing device for supplying or dispensing the active substance is operated at the same time as operating the application tools, for example through the application tools acting on the dispensing device, for example by way of exerting a pressure, preferably on a supply container with the substance. Alternatively or in addition thereto, it can be envisaged that the dispensing device for supplying the substance is operated independently and separately from the application tools.

The device may prevent the tissue from moving out of the way due to its elasticity and flexibility when placing the application tools on the tissue surface in that the tissue is pre-tensioned by the distal tool ends of the application tools. A high and, more particularly, also a low penetration speed of the applications tools is supported. Overall gentle and painless penetration of the organic tissue is facilitated.

The structural design of the device may be such that when moving between the initial position and the penetrating position of the arrangement of application tools, at least one application tool being moved relative to one or more remaining application tools of the arrangement, in terms of its applied application force acts contrary to the action direction of an application force provided by another application tool of the arrangement. In a breakdown of the force components, two parallel, but oppositely directed force components can thus be present, namely a force component of the application force of the at least one application tool and an opposing application force of the other application tool.

In operation, the opposing directions of action of the provided application forces as well as the fact that in a possible embodiment the at least one and the other application tools cross, at least in the penetration position, mean that in another embodiment at least their distal tool ends move away from each other on transition into the penetration position, which results in tensioning of the tissue surface before and optionally also during the penetration. In still another embodiment, rear prolongation lines of the distal tool ends of the application tools cross each other.

It is to be appreciated that in the embodiments which during operation move the arrangement of the application tools from the initial position into the penetration positions, tensioning of the surface of the organic tissue occurs, which supports as gentle penetration of the tissue as possible. In the case of penetration of human skin, this manner of guiding the application tools is perceived as being relatively painless. This painless penetration of the skin can also prove to be advantageous, for example when penetrating human or animal skin during tattooing or administering medicinal products.

When using the device for penetrating the organic tissue, after applying the distal tool ends of the application tools to the organic tissue and operating the operating mechanism for the relative movement from the initial position into the penetration position, the application tools may be assigned to an effect area. The effect area of an application tools extends over the surface section of the organic tissue in which the application force introduced by the relevant application tool acts on the tissue surface, more particularly in the form of superficial tissue displacement. The effect areas for the application tools of the arrangement overlap in the device at least in the case of application tools assigned to each other, so that the opposing directions of action of the application force of the application tools assigned to each other bring about opposing effects in the overlapping effect area, for example opposing forces for skin surface displacement. Preferably these application forces of adjacent application tools operating contrary to each other are essentially cancelled out so that superficial displacement of layer of the organic tissue, for example the skin, is prevented, or at least largely reduced. Preferably the application of two oppositely operating application tools placed adjacent to each other on the tissue essentially cancel each other out on the organic tissue so that superficial displacement of layer of the organic tissue, for example the skin, is prevented, or at least largely reduced.

The application tools are connected to the operating mechanism in such a way that they can be functionally used by operating the mechanism either by hand or by means of a mechanical actuator. The mechanical actuating mechanism, which uses an electric motor for example, can itself be detachably assembled on the operating mechanism.

The operating mechanism may also be self-triggering, for example through a pre-tensioned tool being released from the pre-tensioned position.

The operating mechanism may be configured to move jointly several or all application tools between the initial position and the penetration position. Moving several groups of application tools can also be envisaged.

Several or all distal tool ends of the application tools may be provided with a penetrating device. The penetrating device is configured for opening the organic tissue by means of a cutting and/or piercing movement. In the embodiment, in which not all application tools are provided with a penetration device, some or all of the remaining application tools can be blunt in the distal end area.

In the arrangement of application tools the distal tool ends of the application tools can be arranged along one alignment line, which can be a straight light or a curved line, more particularly a circular line.

The at least one and the other application tools may cross when moving into the penetration position. In this embodiment the crossing of the at least one application tool that is being moved relative to the remaining one and the other application tools from the arrangement, takes place on the movement path to the penetration position, preferably on the second half of the movement path. The crossed arrangement of the application tools is then also retained in the penetration position. It can also be envisaged that the at least one application tool and the other application tools already cross in the initial position. In this embodiment the distal tools ends, at least the tips of the tool ends, are moved away from each other during the movement into the penetration position so that the distal tool ends move apart to tension or stretch the organic tissue in the application area during operation. With regard to the crossed arrangement of the at least one and the other application tools, it can be envisaged that the crossed arrangement in one embodiment is only brought about when the application tools leave a device housing through a housing opening when moving into the penetrating position. A housing of this type can be provided, in particular, in a device which has a manual actuator. The application tools or rear prolongation lines of the distal tool ends are not crossed within the device housing, only outside it.

On moving to the penetration position the at least one and the assigned application tool may be guided laterally displaced with regard to each other. With regard to an alignment line of the distal tool ends of the application tools, more particularly the distal tips, in this embodiment lateral displacement is already present during the movement into the penetration position, thus not only in the penetration position itself. It can also be envisaged that the lateral displacement of the application tools assigned to each other is already present in the initial position.

In another embodiment, by means of the operating mechanism, the movement between the initial position and the penetration position can be carried out repeatedly. The repeatability of the movement means that the arrangement of application tools can be moved between the positions several times and repeatedly. A disposable clip used for a one-off attachment, for example, would behave differently from this. The repetitive movement is carried out, in a particular embodiment, by a device which has mechanical actuator, such as for example a hand-held device for tattooing or for applying permanent make-up. The repeated movement is also carried out by a device when extending, for example, a hollow needle, which can be used for administering a vaccine.

A path of movement when moving the at least one application tool relative to the remaining application tool(s) of the arrangement may comprise a circular path movement and/or a straight movement. The circular or circular section movement can be carried out in the form of a rotational or pivoting movement, for which the at least one application tool is then connected to the operating mechanism in a rotatable or pivoting manner. A straight-line movement can be envisaged particularly in connection with a straight (not bent) needle or a group of such needles for the movement between the initial position and the penetration position. Needles can be held in an assigned needle guide, for example.

The penetration device of the at least one application tool, at least in a last section of the movement to the penetration position, may be guided along a direction of movement which is at an angle, differing from a right angle, to a support surface assigned to one of the distal tool ends of the application tools when in operation. When using the hand-held device the support surface is formed by the surface of the organic material. Applying the penetration device at the distal tool end to the organic tissue at an acute angle supports as gentle penetration of the penetration device into the tissue surface as possible. In the case of a curved line movement towards the tissue surface, the acute angle refers to the acute to the angle between the tissue surface and the tangent on the movement path.

During the movement between the initial position and the penetration position, the at least one application tool may be guided at least in sections in an assigned tool guide. For example, in one embodiment, the holding and guiding of individual needles or groups of needles in a needle guide can be, for example, in groove-like or channel-like recesses. Guiding can be provided along the entire path between the initial position and the penetration position or on just one or several partial sections of this path.

The at least one application tool or the assigned application counter-tool may be provided with a comb component on which several application elements are arranged next to each other. In one embodiment, the several applications elements arranged next to each other each have a penetration device. For example, in one embodiment, the comb elements can also have a penetration device. In another embodiment, two oppositely arranged comb components engage in a crossed manner at least in the penetration position. This results in the surface of the tissue to be penetrating being tensioned or stretched over the entire comb width when the comb sections are moved into the penetration position when using the hand-held device. In one embodiment, the device has two application tools, both designed as comb components, in which all the distal tool ends each have a penetration device. In a further embodiment, a device is provided with two application tools each of which are designed as a multiple-row comb component, whereby in still a further embodiment all the distal tool ends each have a penetration device, for example in the form of a needle point. In the field of tattooing, multiple-row needle arrangements are also known as a "magnum" arrangement.

The path of the displacement movement of the at least one application tool may be adjustable. Adjusting the path of the movement can be used to adjust a penetration depth in the organic tissue to be penetrated in accordance with the application.

A tissue contact or tissue guide surface may be formed in the area of the arrangement of the application tools and/or adjacent thereto. If the application tools are arranged in a device housing, such tissue contact or tissue guide surfaces could, for example, by formed adjacent to a device opening through which the application tools leave the housing when moving into the penetration position. In particular, the tissue contact or tissue guide surfaces serve to improve the guidance of the hand-held device over the surface of the organic tissue to be penetrated. In another embodiment, the tissue contact or tissue guide surfaces are formed with recesses or cut-outs, for example for accommodating tissue folds which may temporarily form in the surface region when using the hand-held device for penetrating the organic tissue. In one embodiment, the tissue contact or tissue guide surface is adjustable, by way, for example, of a relative displacement with regard to the device housing. In another embodiment, such surfaces can be extended and retracted. In another embodiment, the tissue penetration restraint is also produced together with the tool guide.

The application tools in any of the disclosed arrangement embodiments may be formed on a joint basic component. In any of the disclosed arrangements, the application tools can be produced with a ring needle, a ring hollow needle or using a ring flat material. In still other embodiments, two application tools can, for example, be produced at the ends of a wire bow which is held in a housing in such a way that by pressing the wire bow together, either by hand or by means of a mechanical actuator, the application tools formed at the ends are moved from the initial position into the penetration position. Thus, for manual operation, in one embodiment a device with a flat housing can be produced at the sides of which bow sections project which the user can press together by hand, i.e. by means of two fingers, whereupon at the lower side of the housing the two application tools for penetrating the organic tissue are extended in such a way that they cross at least in the penetration position.

The distal tool end of the application tools may be partially or fully retracted into a device housing, at least in the initial position. An embodiment of this type can be provided both in a mechanically-driven device as well as in a device in which the operating mechanism is operated by hand, i.e. manually. In this way, a possible disruptive effect of the distal tool ends of the application tools when outside the housing in the initial position is thereby diminished. For example, complete retraction of the application tools into the device housing supports slight movement of the hand-held device over the surface of the organic tissue. Snagging due to the distal tool ends getting caught on the tissue is prevented. In this way, the risk of injury when the hand-held device is not being used is also reduced.

A mechanical actuating device may be connected to the operating mechanism which is configured to repeatedly carry out the displacement movement of the at least one application tool between the initial position and the penetration position at an operating frequency. In one embodiment, the operating frequency is adjustable. The device with the mechanical actuating device makes it possible for the organic tissue, for example, skin, to be consecutively pierced or cut open several times, especially also for area application. Before, during and/or after penetration of the organic tissue, an active agent or a substance, for example a dye, a coloring agent or pigment, a cosmetic and/or a medical active substance can be applied to the area in which the tissue openings are produced, which can then penetrate into, for example, human or animal skin by way of the tissue openings produced with the aid of the device. The adjustability of the operating frequency supports optimized application for different active agents.

The above explanations apply accordingly in connection with the method of repeated piercing of an organic tissue. The method can be implemented as a method dispensing a substance by way of the device for applying an active substance onto or into an organic tissue.

More particularly, in the meaning used here the term organic tissue covers tissue forms in the following group: tissue layers, skin (epidermis and/or dermis), mucous membrane, endothelium, vascular walls and their layers (intima, media, adventitia), meninx, pericardium, periosteum, peritoneum and other serous skin, joint capsules, inner and/or outer lumina of surfaces of adjoining tissues layers, irrespective of whether these can be reached via a natural or artificial access, animal tissue, human tissue, biological tissue and implantable materials.

Penetration of organic tissue to apply one or more substances can be used in many fields of application. For example, in the field of body art, more particularly the introduction of dyes, pigments or coloring agents into the skin in the case of tattooing of permanent make-up. Cosmetic substances can also be applied, for example bleaching agents or substances to prevent skin ageing (anti-ageing substances) or to reduce wrinkles, such as Botox or skin-tautening lotions. Furthermore, the application of medicinal substance onto or into an organic tissue, more particularly the skin such as for epidermal insulin therapy or mesotherapy, for example, can also be envisaged.

Manual or mechanical single penetration of tissue, more particularly skin, for example in an epidermal or intradermal vaccination, hyposensitisation or diagnosis test procedure, for example in the PRICK test for allergies, can be used painlessly, without blood, with less irritation of the skin and with increased meaningfulness or reliability of the procedure, irrespective of the skill of the user.

With the aid of the device, in one application hair follicles may be implanted. Here the hair follicles are inserted from the dispensing device into the tissue openings produced by the penetration device.

On one side of the alignment line the application tools can also be blunt and only act as a holding or tensioning element on the tissue on this one side, whereas only the tools on the opposite side and essentially acting in the opposite direction are sharp and can penetrate into the tissue.

In the projection plane perpendicular to the action direction of the application tools, an angle $\alpha$ enclosed by oppositely acting application tools can be less than 180° and greater than 0°, and in a preferred embodiment between 130° and 150°. An acute angle $\beta$ between the application tools acting on the organic tissue and the tissue surface can be of identical or different size on both sides.

A plurality of application tools aligned next to each other on both sides along the aforementioned alignment line and acting in opposite force directions may each form a tool comb, whereby the alignment line or the course of the tips of the tool comb can be straight or defined by straight lines arranged at angles with regard to each other, and, on the other hand, can also be singly or multiply bent. Immediately before penetration, on contact with the tissue the tool tips of the application tools are preferably positioned either in front of or behind the alignment line, or directly on the alignment line. In a further embodiment, the tool combs applied to a tool carrier can be made of individual application tools or each designed as one piece.

The penetration devices may be, for example, in the form of needles or micro-needles, whereby hollow needles can also be used. Blades running perpendicularly to or along the direction of action of the force of the assigned application tools can be used for cutting the tissue. Bifurcation needles can also be used.

A manually operated application device can have two operating arms which are springingly arranged in a V-shape and operated by the user's fingers, and which have application tool holders on their free ends to which application tools are attached. A manually operated device for penetration of this type can be produced with all the functional elements (operating arms, tool holders, penetration device and/or tool combs) but also from one piece, for example a V-shaped, annular or rectangular elastic flat material.

The manually or mechanically actuated operating arms with application tools provided on the free ends can be arranged in a housing. The application tools are, for example, situated in the area of an opening of the housing and are guided on the outer tool guiding elements delimiting the opening, as well as on an inner tool guiding element acting as a penetration block for the tissue. The tissue is fixed between the outer and the inner tool guiding elements in the area of the opening for the application tools, and is tensioned by application tools acting in the opposite direction and also, with restricted penetration depth and penetration speed, can be penetrated with low vibrations during mechanically oscillating repeated penetration. The interior of the housing can be provided with a tank for a substance to be introduced into the tissue at the same time as or deferred with regard to the penetration, such as, for example, a tattooing fluid, a vaccine or other medicinal product to be applied via the tissue.

A manually actuated penetration device designed with a housing can have at least one circular needle which is made of an elastic material and is guided in a flat housing and which at its free ends has formed-on application tools and lateral operating arms. The operating arms of the ring needle project from laterally opposing slits in the housing and the application tools pass through an upper opening of the housing and are guided there on outer tool guiding elements as well as on inner tool guiding elements forming a tissue penetration block. In addition, on the side opposite the application tools the at least one circular needle is guided on outer and inner needle guiding elements. The inner needle guiding elements and the tool guiding elements are connected to each other by bars and with these and the side walls of the housing form the tank for any substance that may possibly be applied onto or into the tissue.

In one embodiment, a mechanically actuated penetration device may have two crossing operating arms that are in active connection with actuation areas on an actuation body applied to an actuation plunger. In this embodiment, the two crossing operating arms can be pivotably borne in a housing against a spring action with actuation areas opposite each other to produce the pre-tensioning and piercing movement.

In another embodiment, a mechanically actuated penetration device may have two operating arms arranged in parallel to each other in a housing and provided with guide pins, and a actuation plunger, with an actuation body at its free end, which oscillates in a housing against a spring force. The guide pins projecting from the operating arms engage in obliquely running guide slots of the actuation body so that the operating arms with the application tools held thereon are alternately moved towards and away from each other in parallel alignment during the back and forth movement of the actuating plunger in order repeatedly insert and retract the application tools or tool combs attached to the tool holders of the operating arms in opposite force action directions laterally into the tissue fixed to the opening of the housing and initially pre-tensioned by the application tools.

In another embodiment of the penetration device, two operating arms can be provided on a base plate arranged at a distance from and in parallel to each other and guided by means of guide bolts in obliquely running guide slots, said arms each having on the outward facing side in the longitudinal direction of the operating arms two oblique actuation areas offset in parallel though the formation of a lug. A U-shaped actuating plunger laterally in contact with the operating arms has oblique actuating areas on the insides of its actuating limbs which are also offset in parallel by a lug, so that the operating arms which are pressed apart by the spring effect, during a back forth movement of the plunger in contact between the contacting oblique actuation areas alternately move towards and away from each other and thus insert and retract the application tools applied at the free ends of the operating arms with the tool tips directed towards each other into the tissue that has been pre-tensioned during penetration.

The device—viewed in the direction of an alignment plane of the tool tips—can have three or more application tools arranged at an angle to each other and working against each other, the tool tips of which act on the tissue before or behind a circular application line, possibly reduced to one point. In the circle application, tools which are offset or opposite each other at an angle $\alpha$ can penetrate into the tissue in essentially opposite directions and after pre-tensioning of the tissue.

At the front, the mechanically actuated penetration device can have application tools, perpendicularly braced by an actuating plunger moving to and fro against a spring force, which are guided between a rotationally symmetrical inner tool guiding element (tissue penetration block) with a convex, vaulted mantle surface, and a corresponding concavely vaulted outer tool guiding element opening into a circular opening. Along a circular alignment line offset application tools opposite each other contact the tissue at an angle $\alpha$ enclosed by these, essentially in the opposite force direction in order to tension and then penetrate it.

Guided in a flat housing, at least one manually operated circular needle can be provided which has operating arms penetrating through laterally opposite slits of the housing and formed on its free ends application tools which are guided in the area of the upper opening of the housing on inner tool guiding element as well as on outer tool guiding elements.

The at least one circular needle can be guided on outer and inner needle guiding elements on the side opposite the application tools, whereby the inner needle guiding elements and tool guiding elements are connected by bars, and with these and the side walls of the housing form the tank for the substance to be applied onto or into the tissue.

In one embodiment, two operating arms pivotably borne in a housing and crossing each other of opposing actuation areas which are in active connection with actuation areas of an actuating body on an oscillating actuating plunger can be provided.

In another embodiment, two operating arms are provided with guide pins and arranged in parallel in a housing, and arranged to oscillate in the housing is an actuation plunger with an actuation body on its free end, whereby the guide pins braced by the operating arms, are engaged by oblique guide slits of the actuation body such that the operating arms with the application tools held thereon can be alternately move towards and away from each other with the to-and-fro movement of the actuation plunger.

On a base plate, at a distance from and in parallel to each other, and guided in oblique guide slits, two operating arms that are elastically pushed apart can be provided, each of which has on the outwardly directed side in the longitudinal direction of the operating arms oblique actuations areas; as can a U-shaped actuation plunger in lateral contact with the operating arms, which has oblique actuation areas on the inner sides of its actuation limbs, so that the elastically pressed apart operating arms alternately move towards and away from each other in the case of a plunger movement due to the contact between the oblique actuation areas.

It can be envisaged that in the rest position the tool end are positioned before and/or behind the alignment line and/or directly on the alignment line.

It can be envisaged that the application tools contacting the tissue on a circular alignment line are perpendicularly braced by the front surface of a circular tool holder held on an actuation plunger and guided in a housing section, and are guided between a rotationally symmetrical convexly vaulted inner tool guiding element and a corresponding concavely vaulted, outer tool guiding element with a round opening.

BRIEF DESCRIPTION OF THE DRAWINGS

Further embodiments are described in more detail below with reference to the figures of a drawing. In these.

LIST OF REFERENCES

Figure 1A:
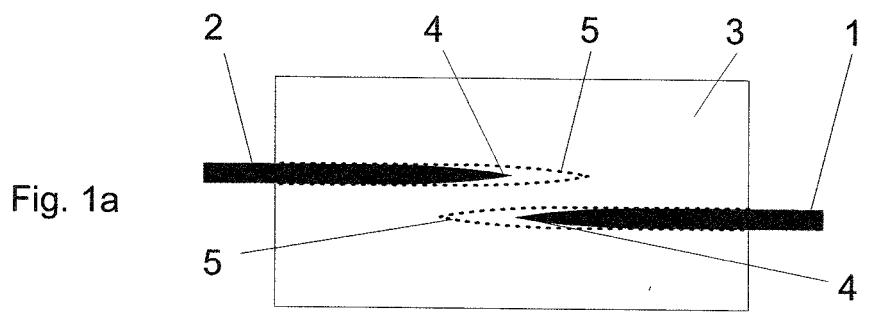
FIG. 1a shows a view from above of two application tools acting on an organic tissue which are opposite and offset with regard to each other on an alignment line.

1 First application tool
2 Second application tool (2a, 2b)
3 Tissue (3a Tissue surface, 3b Application area)
4 Tool ends
5 Penetration channel in the tissue
6 Alignment line/Application 6a of the tool tips
7 Effect area/Skin displacement of 4
8 Overlapping area of 7
9 Tool comb
10 Cutting blade
11 Operating arm
12 Tool holder
13 Housing
14 Circular needle
15 Lateral openings in 13
16 Outer needle guiding element
17 Inner needle guiding element
18 Inner tool guiding element
18a Tissue penetration block
19 Outer tool guiding element
20 Bar between 17 and 18
21 U-shaped actuation plunger
22 Actuation limb of 21
23 Oblique actuation areas of 22
24 Guide slits in 30
25 Guide bolt of 26
26 Operating arms
27 Oblique actuation areas of 26
28 Lugs of 26
29 Lugs of 22
30 Base plate
31 Housing, two-part
32 Actuation plunger
33 Guide pin of 34
34 Actuation element of 32
35 Operating arms
36 Actuation area of 35
37 Tool holder
38 Actuation area of 34
39 Opening in 13, 31
40 Tool guiding element, tissue penetration block
41 Retaining bar (41b)
42 Housing
43 Guide pins of 46
44 Actuation element of 45
45 Actuation plunger
46 Operating arms
47 Tool holder
48 Straight guide slits in 44
49 Guide pins on the housing 42
50 Oblique guide slits in 44
51 Cylindrical housing
51a First housing section
51b Second housing section
52 Actuation plunger
53 Circular tool holder
54 Inner tool guiding element
55 Round opening
56 Outer tool guiding element
57 Pressure spring
60 Dispensing device
61 Storage container
62 Dispensing component
63 Openings in the dispensing component 62
64 Fluid pipeline
70 Holder
β Acute angle between 1,2 and 3a
α Angle between 1 and 2
A Tissue surface

DETAILED DESCRIPTION

Figure 2:
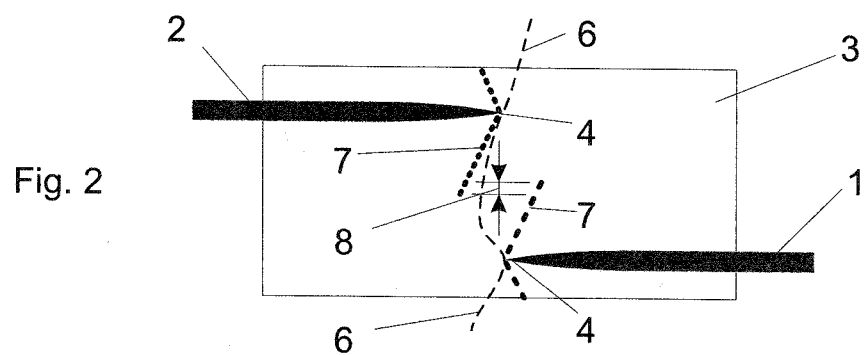
FIG. 2 shows a schematic view according to FIG. 1a for the definition of a lateral distance between two adjacent application tools opposite each other.

FIGS. 1 to 3 show a view from above of various embodiment variants of tool arrangements of a device for penetrating an organic tissue and applying an active substance onto or into an organic tissue. As depicted, at least two pointed and/or sharp, piercing and/or cutting—first and second application tools 1, 2 are provided facing each other in pairs, but slightly offset with regard to each other such that during penetration the application tools 1, 2 move towards each other at an angle α through opposing force effects. It is to be appreciated that after application to the tissue 3, for example skin, in a first movement phase, the application tools 1, 2 initially pre-tension the tissue lying in the effect area of the tips of the tool ends 4 (distal ends) and then at the low speed which is possible, but not necessary, due to the automatic pre-tensioning, penetrate flat into the tissue and produce a penetration channel 5 or slit. The tips of the tool ends 4 are arranged on a tissue surface 3a in an application area 3b.

Figure 3A:
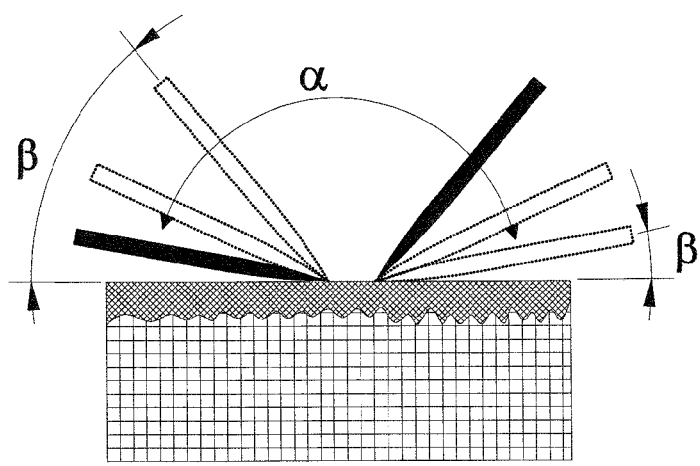
FIGS. 3a-3c shows side views of two application tools in contact with an organic tissue, more particularly skin, at different angles with opposite tool tips offset at a distance before/on/behind a joint alignment line.
Figure 3B:
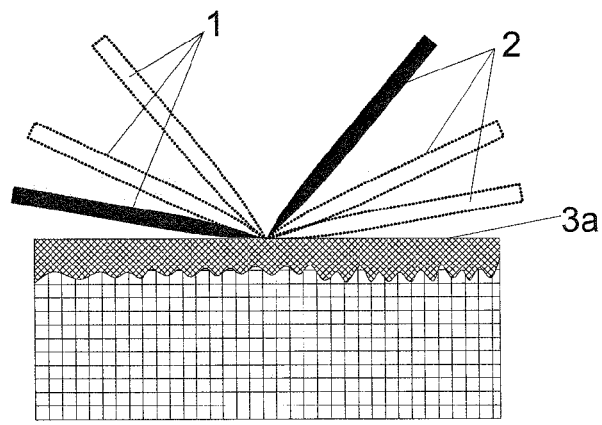
Figure 3C:
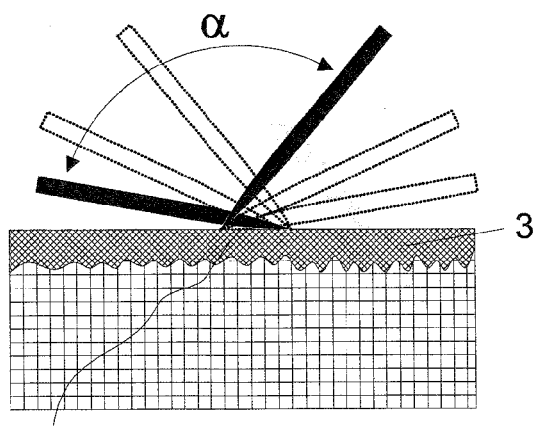
Figure 4A:
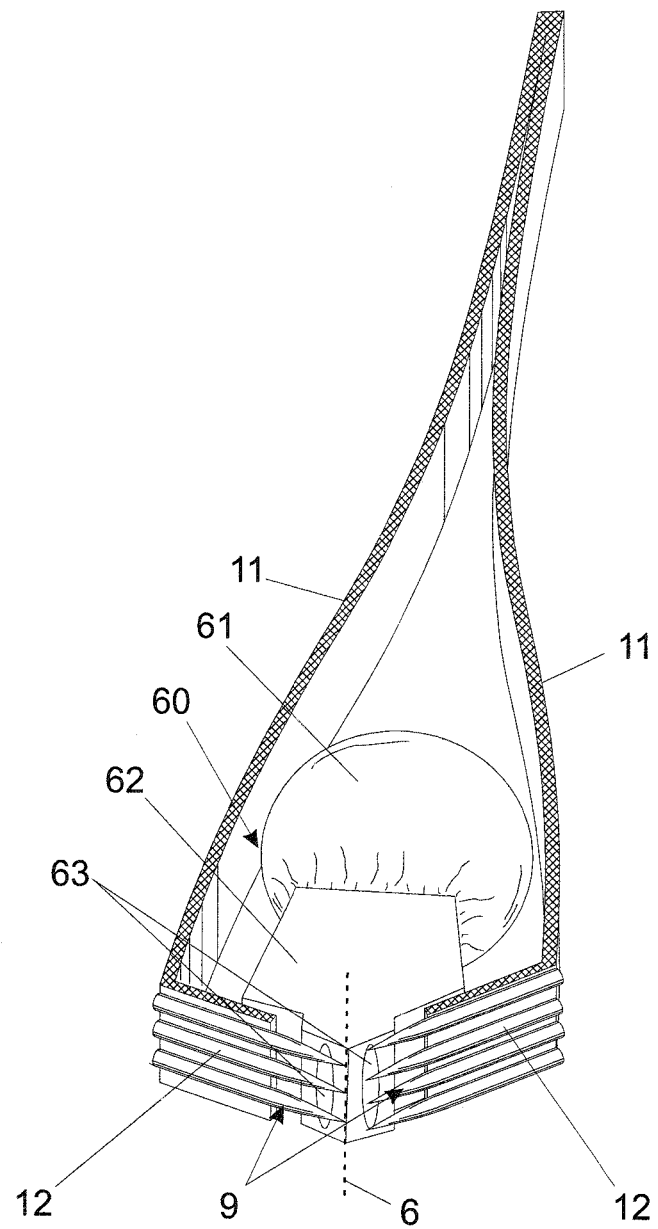
FIG. 4a shows a perspective view of a manually operated hand-held device with several application tools arranged opposite and offset with regard to each other and held on tool carriers with sprung operating arms, whereby a storage container of a dispensing device is arranged between the application tools.
Figure 4B:
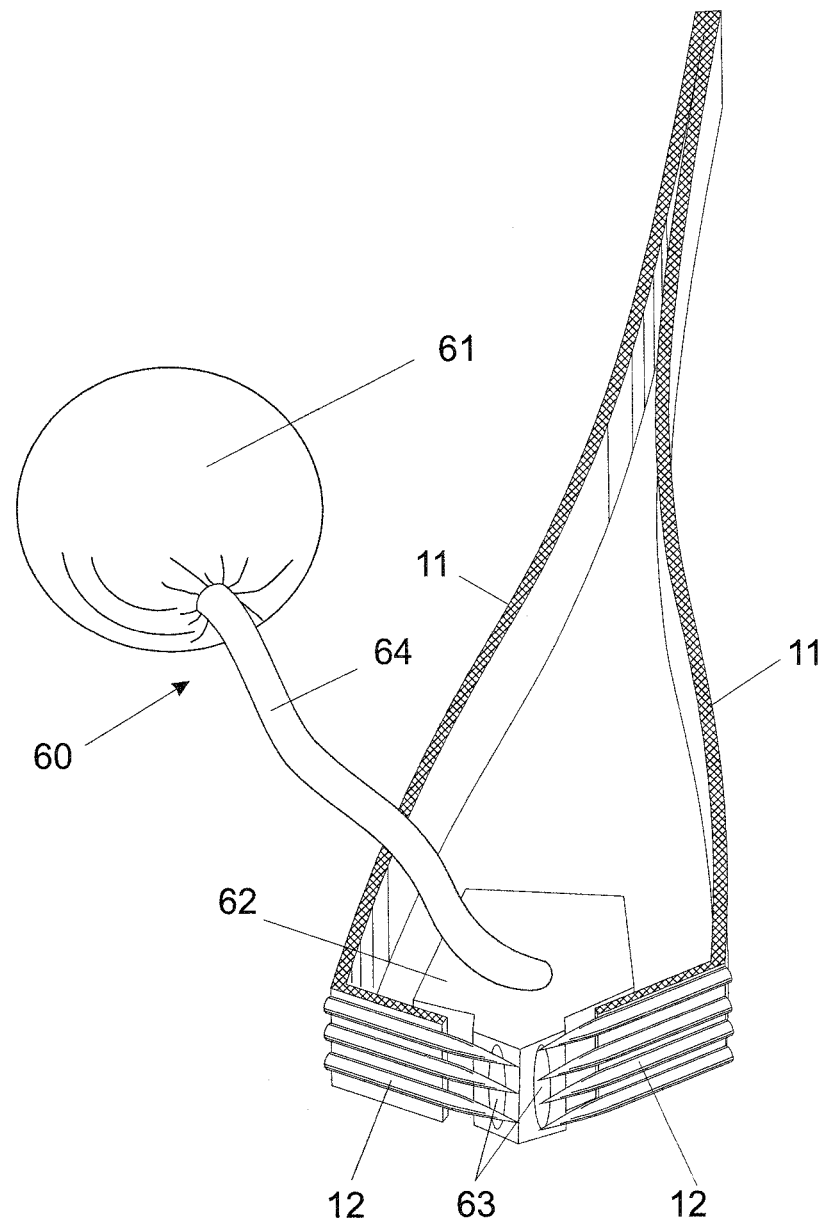
FIG. 4b shows a perspective view of a manually operated hand-held device with several application tools arranged opposite and offset with regard to each other and held on tool carriers with sprung operating arms, comparable with the embodiment in FIG. 4a, whereby in contrast to the latter a storage container of s dispensing device is arranged outside the application tools.
Figure 4C:
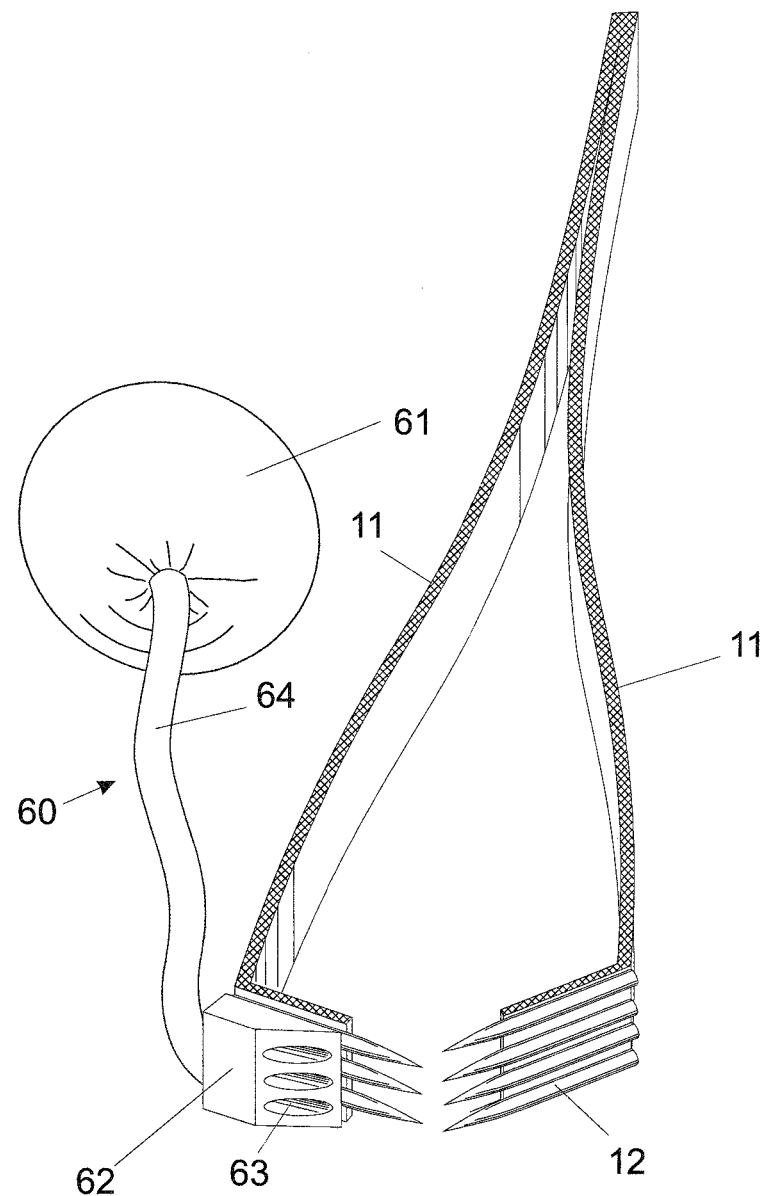
FIG. 4c shows a perspective view of a manually operated hand-held device with several application tools arranged opposite and offset with regard to each other and held on tool carriers with sprung operating arms, comparable with FIG. 4b, whereby in contrast to the later the substance is dispensed on the tissue side of the tools.
Figure 5C:
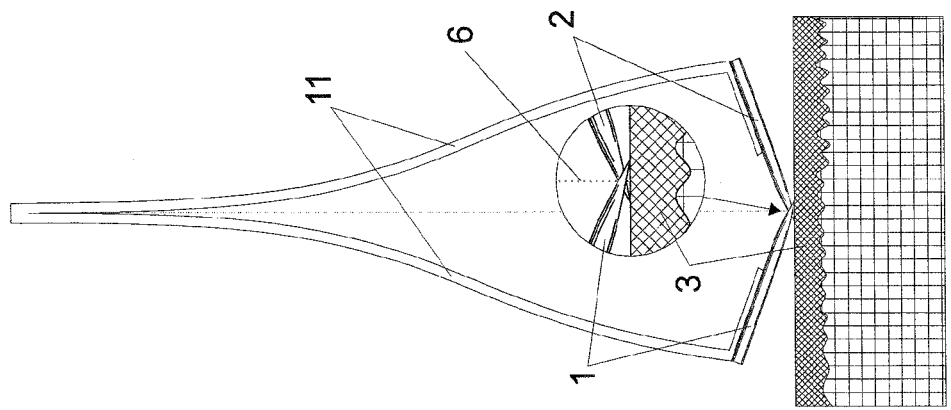
FIGS. 5a-5c show side view of the hand-held device in accordance with FIG. 4 placed on the tissue in different positions in accordance with FIG. 3, FIGS. 6a-6d show embodiment variants of application tools with tool combs as distal tool ends on a basic component, each produced in one piece from an elastic flat material.
Figure 5B:
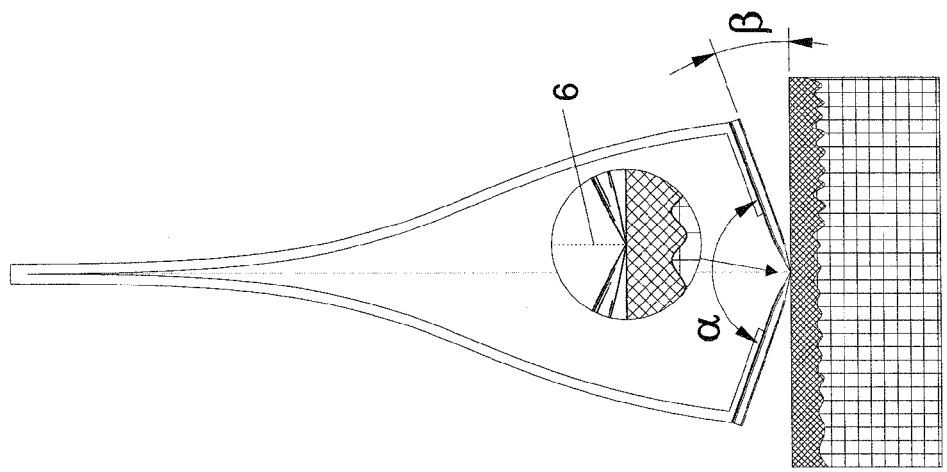
Figure 5A:
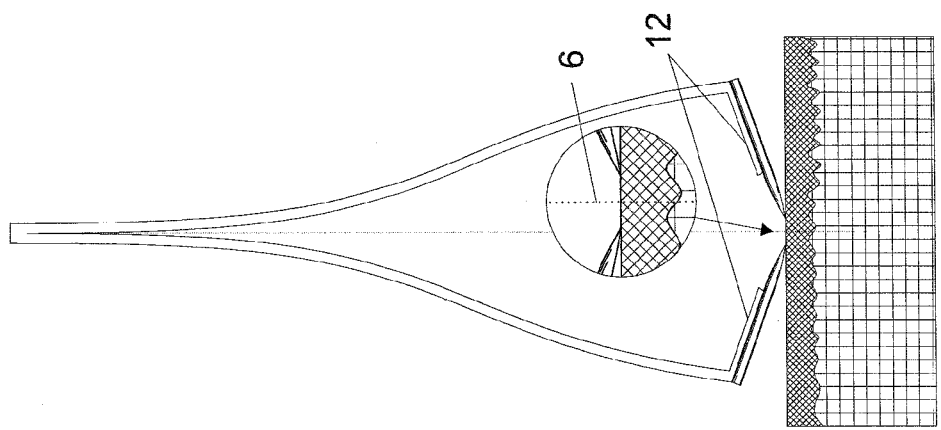
Figure 6A:
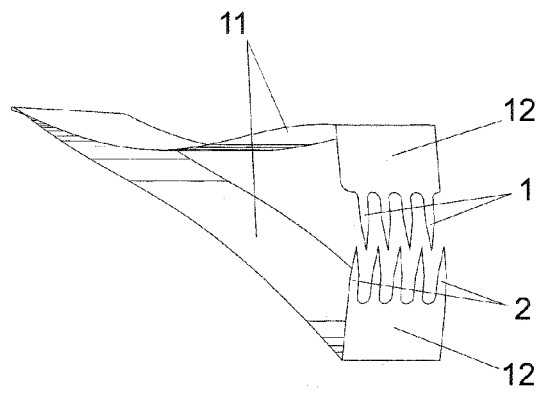
Figure 6C:
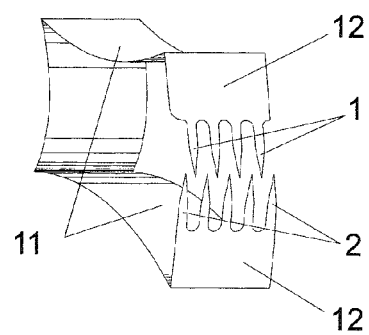
Figure 6B:
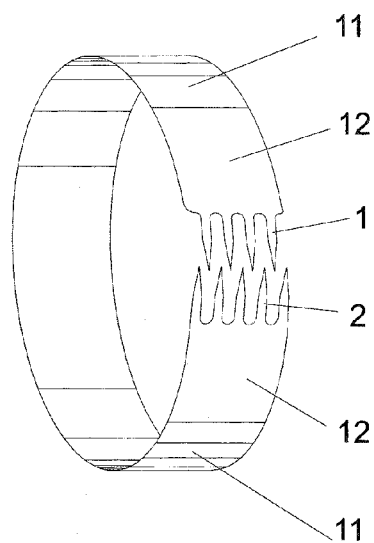
Figure 6D:
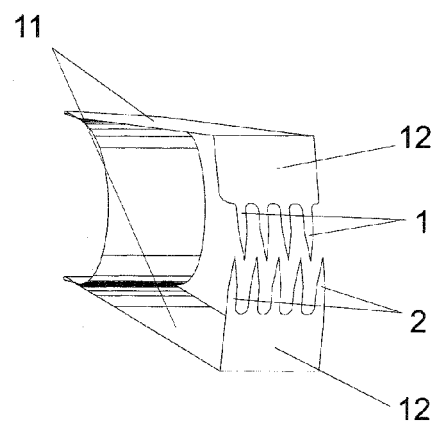

In the schematic view in accordance with FIGS. 1a, 2 and 3b, on application to the tissue the tips of the tool ends 4 are at the same level as the penetration device of the two application tools 1, 2, i.e. on a joint alignment line 6. However, in the initial position, the tips of the tool ends 4 can also be before (FIG. 3a) or behind this common alignment line 6 (FIG. 3c). As shown in FIG. 2 the lateral distance between two adjacent (opposite) tool tips 4 is so small that adjacent effect areas 7 of the tool tip 4 form a joint overlapping area 8. This ensures that due to the oppositely directed force effect of adjacent tool tips 4 the tissue is pre-tensioned before piercing.

As shown in FIGS. 3a to 3c, the oppositely directed application tools 1, 2 can be aligned with regard to the surface of the tissue at different acute angles β or—as showed with the dotted lines—also at a correlating angle. In the projection plane perpendicular to the effect direction of the application tools, the angle α enclosed between the oppositely directed application tools 1, 2 is less than 180° and greater than 0° as shown in FIGS. 3a to 3b, and is, as shown by the applications tool 1, 2 closest to the tissue 3 in the drawing, preferably between 150° and 130°. The penetration depth of the application tools into the tissue is decisively determined by the angles α/β.

Figure 1B:
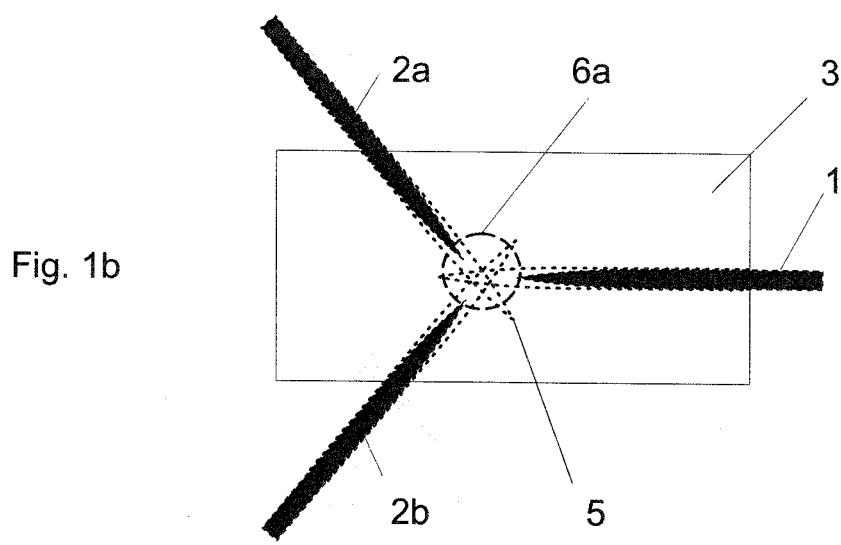
FIG. 1b shows a variant embodiment of the tool arrangement according to FIG. 1a in which one application tools is replaced by two applications tools arranged at an angle.

In FIGS. 1a, 2 and 3a to 3b, in order to explain a pre-tensioning principle occurring in several embodiments, only one pair of opposite and laterally offset applications tools 1, 3 is shown. FIG. 1b shows an extended form of embodiment of a tool pair, in which in a view from above two second application tools 2a, 2b arranged at an angle with regard to each other are opposite the first application tools 1. In this case the tips of tool ends 4 of three application tools 1, 2a, 2b acting in an offset manner on the tissue are arranged on a circular to punctiform application line 6a or cross each other (not shown) behind this alignment line 6a.

As shown in FIGS. 4, 6, 7a and 7b, in the shown example of embodiment on each side of the alignment line 6 there are several offset and opposite application tools 1 and 2, which form a tool comb 9 in each case. The common alignment line 6, on which the opposite application tools 1, 2 of tool combs 9 are aligned, can be straight or curved or also include two or more straight lines arranged at an angle. It is also conceivable for an application tools or application comb to be arranged only on one side, with a holding tool (not shown) or tool comb without penetrating tool ends that pre-tensions the tissue being provided on the opposite side.

In accordance with FIGS. 1 to 3, and in FIGS. 4, 5, 8, 9, 13 and 15 explained below, the application tools 1, 2 are in the form of pointed needles with a circular cross-section. However, the application tools 1, 2 can also be hollow needles/cannulas (not shown), or have a flat cross-section with a point (FIGS. 6a-d, FIG. 12a-b), or a sharp blade, or, in accordance with FIGS. 7a and 7b, they can be designed as longitudinal knives or blades 10 for penetrating the tissue, more particularly the skin, by means of longitudinal slits, or as distal tools ends that are blunt on one side.

An essential area of application of the penetration device with the tool arrangement explained with the aid of FIGS. 1 to 3, is the penetration of tissue for the simultaneous or time-deferred introduction of certain cosmetic or medicinal substances into or onto the tissue or into the body or an organ via the tissue.

The manually operated device shown in FIGS. 4a to 4c and 5 comprises two connected, elastically sprung operating arms 11 with tool carriers 12 projecting from their free ends and attached thereto applications tools 1, 2, here in the form of pointed needles and each forming a tool comb 9. After applying the tip of the tool ends 4 (distal tool ends) to the tissue, the operating arms 11 are pressed together with the fingers, whereby the application tools 1,2 are pushed into the simultaneously pre-tensioned tissue in opposite directions at an acute (obtuse) angle β with a penetration depth corresponding thereto. After releasing the operating arms 11, the application tools 1, 2 or tool combs 9 return to the initial position and the procedure can be repeated as often as required.

A dispensing device 60 for supplying the substance to be applied can be arranged between the operating arms 11, for example (cf. FIG. 4a), so that by actuating the operating arms 11 the substance, which is provided in a storage container 61, is released. The storage container 61 is in fluid connection with the dispensing component 62, which has opening 63 for supplying the substance to the application tools. In this way a medicinal product, for example, can be administered via the skin, or a tattooing fluid applied to the upper layer of the skin. The dispensing device 60, or at least the storage container 61, can however also be attached outside the operating arms 11 (cf. FIG. 4b). In one embodiment (cf. FIG. 4c), the substance flows along the tool carrier 12 to the penetration area.

FIGS. 6a to 6d show embodiment variants of application tools with tool combs as distal tool ends which are formed in each case in one piece from a V-shaped, circular or trapezoidal flexible flat material. For example, a metal strip can form the operating arms 11, the tool carrier 12 and the application tools 1, 2 or the two tool combs, or at least one tool comb which is capable of penetrating the organic tissue. These one-piece application devices can either be operated manually or can be integrated into mechanically actuated device.

Figure 7A:
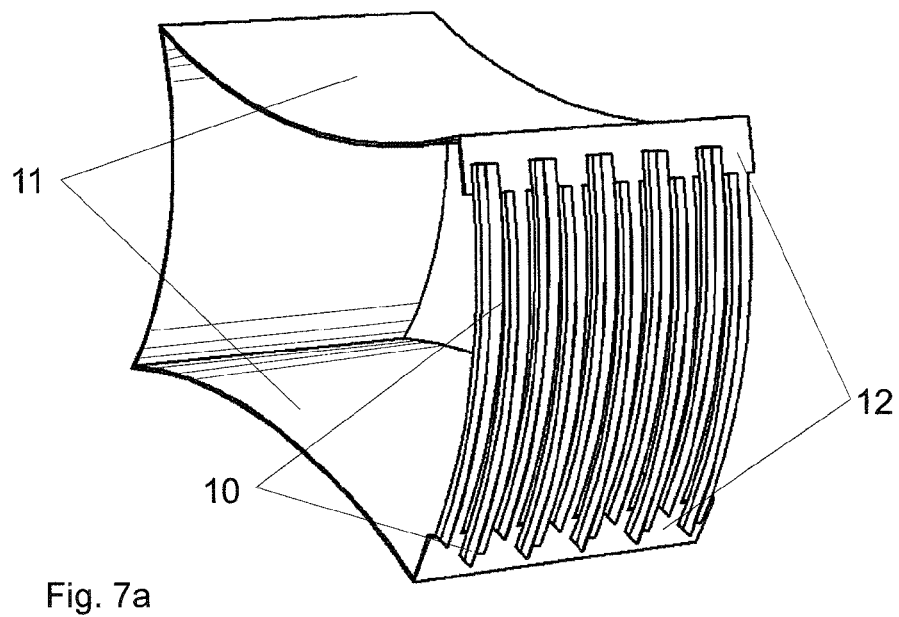
FIGS. 7a and 7b show an embodiment variant of a cutting tool in comb form on a basic components made of an elastic material, in an initial position (FIG. 7a) and in a penetration position (FIG. 7b)
Figure 7B:
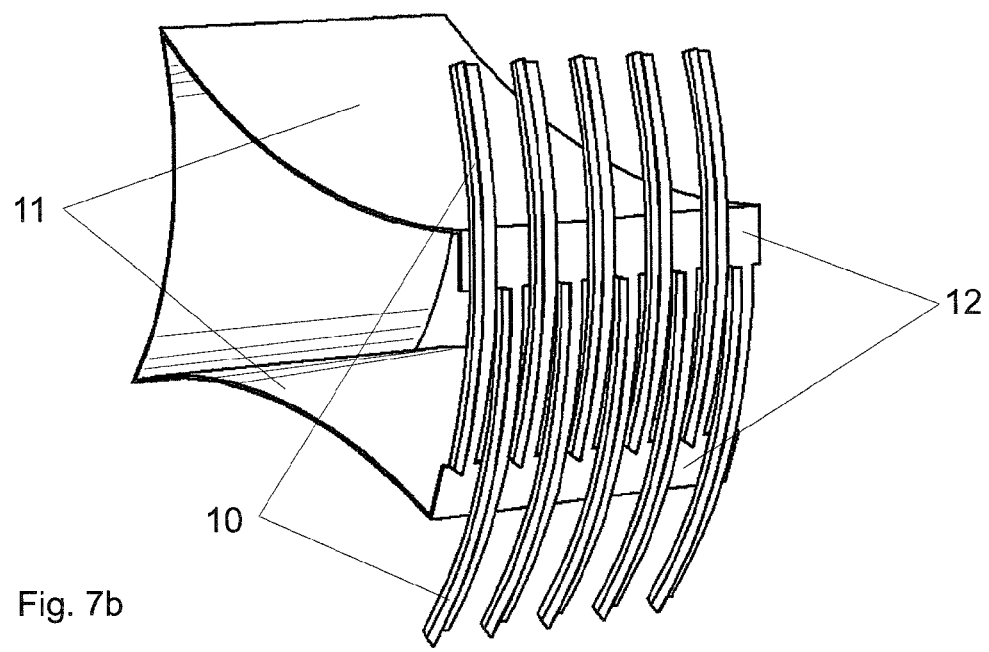

The device shown in FIGS. 7a and 7b (in the initial and penetration position) is also produced with a flexible metal strip. However, in this case the application tools formed on the tool carrier 12 are designed as blades 10 for opening the skin by means of slits for the simultaneous or time-deferred application of a substance into the skin or the tissue.

Figure 8:
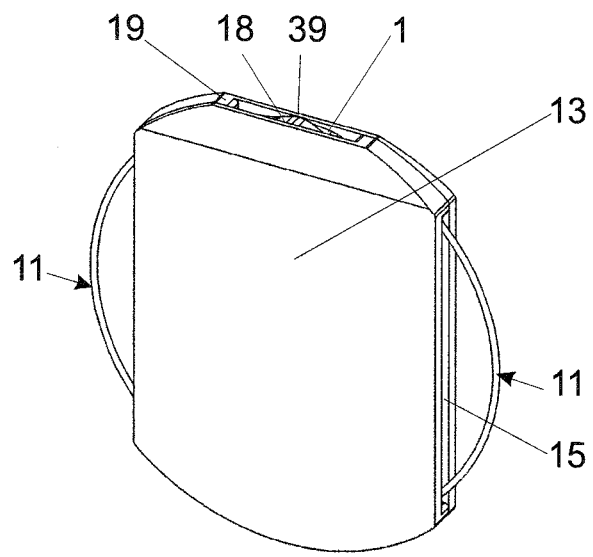
FIG. 8 shows a perspective view of manually operated hand-held device with an elastically deformable ring-shaped tool carrier guided in a housing.
Figure 9:
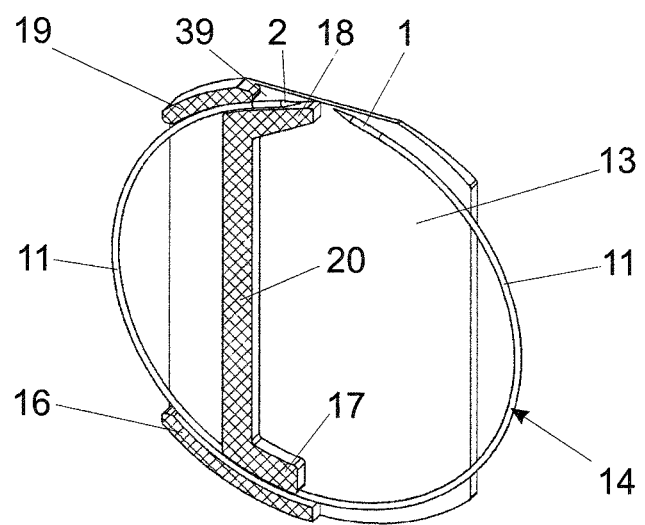
FIG. 9 shows an internal view of one half of the housing of the device in accordance with FIG. 8.

FIGS. 8 and 9 show an embodiment variation of a manually operated device provided with a housing, which is designed as a flexible, open circular needle 14 with lateral operating arms 11 which project through lateral openings 15 of the housing 13 in the form of lateral slit openings and have application tools 1, 2 formed on their free ends. On the side opposite the application tools 1, 2, the circular needle 14 is guided between outer and inner needle guiding elements 16, 17. The application tools 1, 2 of the circular needle 14 are held between inner tool guiding elements 18 and outer tool guiding elements 19, which are at a distance from one another, thereby forming an opening 39 in the housing 13. As shown schematically in FIG. 10, when using this penetration device the two outer tool guiding elements 19 are supported on the tissue surface A, while the area of tissue A1 lying between them is held on the inner tool guiding elements 18 lying further inwards and acting at the same time acting as a tissue penetration block (18a in FIG. 10). Located on or in the housing is a storage tank (not shown) for the substance(s) to be applied which through operating the application tools release the substance to be applied in such a way that the substance reaches the penetration area (in the vicinity of the opening 39). However, the circular needle can also be designed as a hollow circular needle and in this case be directly connected to the dispensing device so that on operating the device the substance to be applies is dispensed via the hollow needle.

Figure 10:
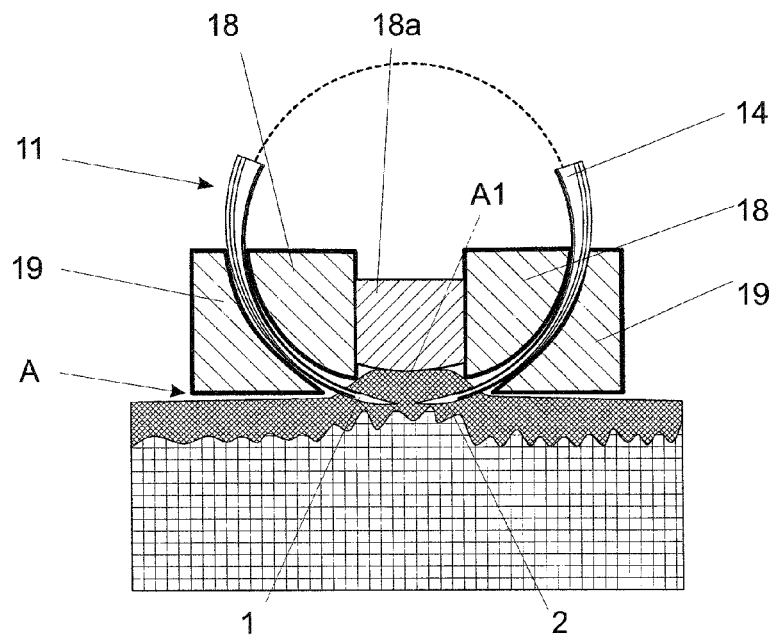
FIG. 10 shows a functional diagram of the device shown in FIGS. 8 and 9 with an adjustable tissue penetration block.

The tissue penetration block 18a shown schematically in FIG. 10 can be arranged in an adjustable manner in order to be able to set the penetration depth of the tissue into the opening and thereby the vertical piercing depth of the application tools 1, 2 into the tissue. On operating the device, via the two operating arms 11 laterally projecting from the housing 13 via the opening 39, the tissue is fixed between the outer tool guiding elements 19 and the inner tool guiding elements 18 (tissue penetration block 18a) and pre-tensioned by the application tools 1, 2, which are offset with regard to each other and act on the tissue in opposite directions, so that the application tools can penetrate into the tissue with a small vertical piercing depth.

In FIG. 9, for the sake of simplicity only one outer and inner tool guiding element and/or needle guiding element 16 to 19 is shown, the corresponding or complementing structures are produced by the half of the housing, which is not shown and is preferably identically manufactured. The inner tool and needle guiding elements 17, 18 can each be connected via a bar 20 in order, together with the inner surface of the housing 13, to form a small tank, which is then part of the dispensing device 60, for holding a tattooing agent, a pharmaceutical product or suchlike. When using a solid circular needle, via a small opening between the two inner tool guiding elements 18 a vaccine, a tattooing agent or suchlike can emerge from the tank before or during operation and penetrate into the tissue after or with the piercing procedure. In addition, when using hollow needles as the circular needle 14, the needle lumens can be connected to the tank in the area of the corresponding inner needle guiding elements 17.

Figure 11A:
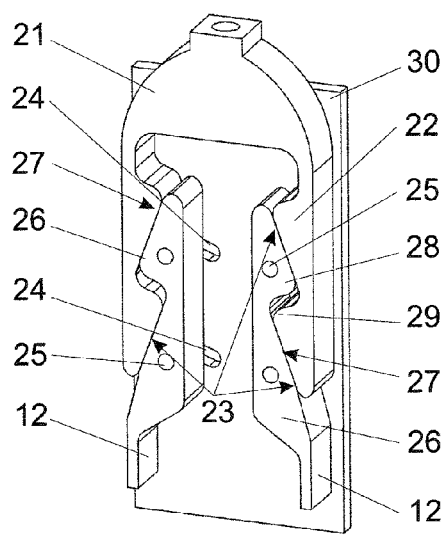
FIGS. 11a and 11b show a form of embodiment of an operating mechanism for application tools with a tool carrier operated by mechanically actuated plunger in a position before piercing (initial position) (FIG. 11a) and after piercing (penetration position) (FIG. 11b) the tissue.
Figure 11B:
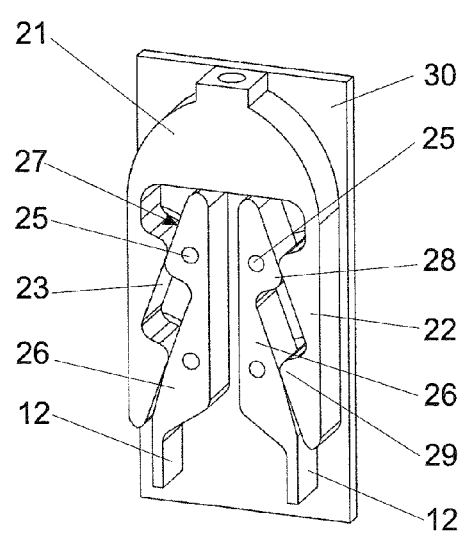

FIGS. 11a and 11b show an embodiment of the operating mechanism for the application tools in a position before and after penetration of the application tools (which are not shown here). As an operating element, a mechanically actuated U-shaped actuating plunger 21, which on the inner sides of the two actuating limbs 22 has two oblique first actuation areas 23 offset in parallel by lugs 29, is arranged to move up and down on a base plate 30. The base plate 30 has two pairs of downwardly directed guide slits 24, in which the guide bolts 25 of two operating arms 26 that are arranged at a distance in parallel to one another engage. A tool carrier 12 provided on the lower end of each operating arm 26 serves to attach the application tools or tool combs (not shown) which are offset and aligned opposite each other at a predetermined angle α.

The oblique actuation areas 23 on the actuation limbs 22 interact with second oblique actuation areas 27 of the operating arms 26, which are offset in parallel via lugs 28 and run in the same direction. FIG. 11a shows the actuation plunger 21 in an upper position and the two operating arms 26 in a position in which they are pulled apart by a pressure spring (not shown) arranged between the two operating arms 26, in which position the application tools (not shown in FIGS. 11a/b) do not penetrate the tissue. In the view shown in FIG. 11b, the actuation plunger 21 is in the lower position, whereby during the downward movement of the actuation plunger 21 along the guide slits 24, the operating arms 26 move towards each other such that the application tools thus penetrates into the tissue at an acute angle β to the skin surface.

Figure 12A:
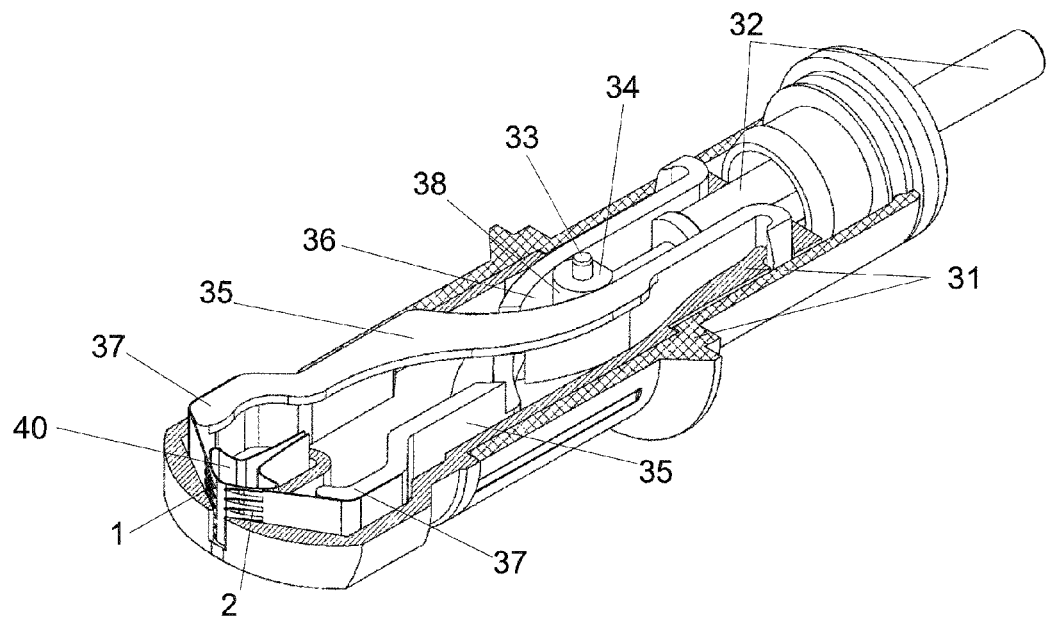
FIGS. 12a and 12b show a further form of embodiment of a mechanically actuated hand-held device in a position before piercing (initial position)(FIG. 12a) and in a position after piercing (penetration position) (FIG. 12b)
Figure 12B:
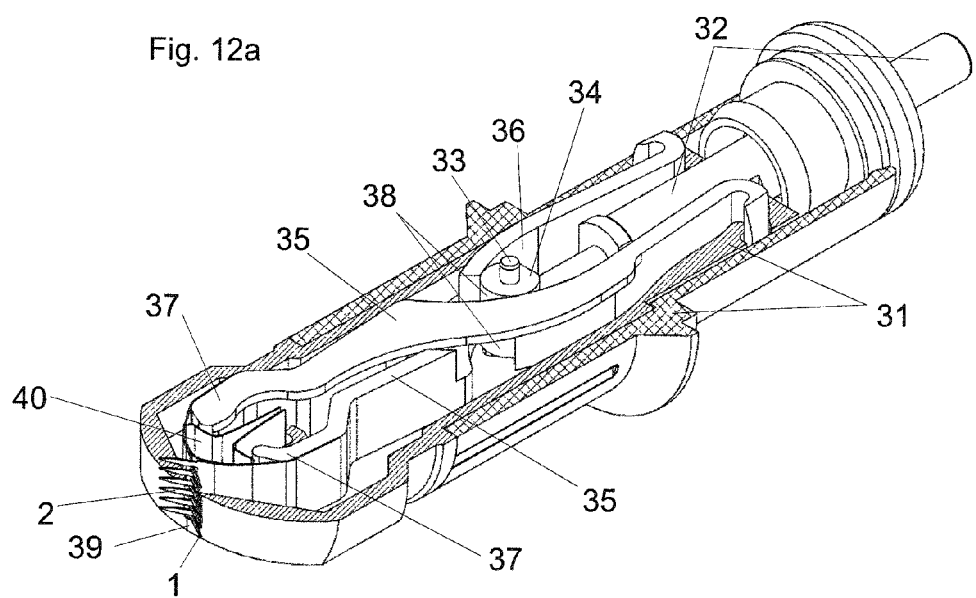

An embodiment variant of a mechanically-actuated device shown in FIGS. 12a and 12b comprises an actuation plunger 32 which is mechanically movable within a two-part housing 31 and has attached to its free end an actuating element 34 guided by a guide pin 33 in guide slits (not shown) of the housing 31. Arranged in the housing 31 are two crossing and pivotable operating arms 35 with, on their inner side, a concavely vaulted actuation area 36 and tool holders 37 formed on the free ends. One actuation area 38 of the actuation element interacts with the vaulted actuation areas 36 provided on the inner sides of the operating arms 35. Attached to the tool holders 37 of the operating arms 35 are oppositely directed, offset, application tools 1, 2, here each in the form of a tool comb, which are guided in an inner tool guiding element 40 (tissue penetration block) provided in the interior of the housing 31 under the slit opening 39. Guide grooves (not shown) can be formed in the tool guiding element 40 for guiding the application tools 1, 2.

On applying the device to the tissue, the tool guiding element 40 acts as a tissue penetration block 18a (FIG. 10) fixing the tissue in a vertical direction in accordance with FIG. 10. When the actuating element 34 is moved forwards along the curved actuation areas 36 of the operating arms 35 the application tools 1, 2 are moved towards each other against the spring force of a pressure spring (not shown) provided between the two operating arms, in order to initially pre-tension the tissue, more particularly the skin and then pierce it. During the return movement of the actuation element 34, the operating arms are pivoted back into their initial position through the spring force and the applications tools are retracted from the tissue.

The module shown in FIGS. 12a and 12b can be connected, for example, through being pushed on or screwed on, to an actuation module (not shown). Such actuation modules are known as such in various embodiments, for example in connection with hand-held devices for tattooing of for applying permanent make-up. Normally, the actuation module provides a linear to-and-fro movement at an operating frequency, which in the embodiment in FIGS. 12a and 12b, is coupled to the actuation plunger 32 that moves back and forth.

A further embodiment of a mechanically actuated device for the repeated penetration of a tissue in order, for example to apply a substance is set out in FIGS. 13a, 13b, 13c and 13d. In a comparable manner with the embodiment in FIGS. 12a and 12b, the shown module can be detachably connected to the actuation device (not shown).

Figure 13A:
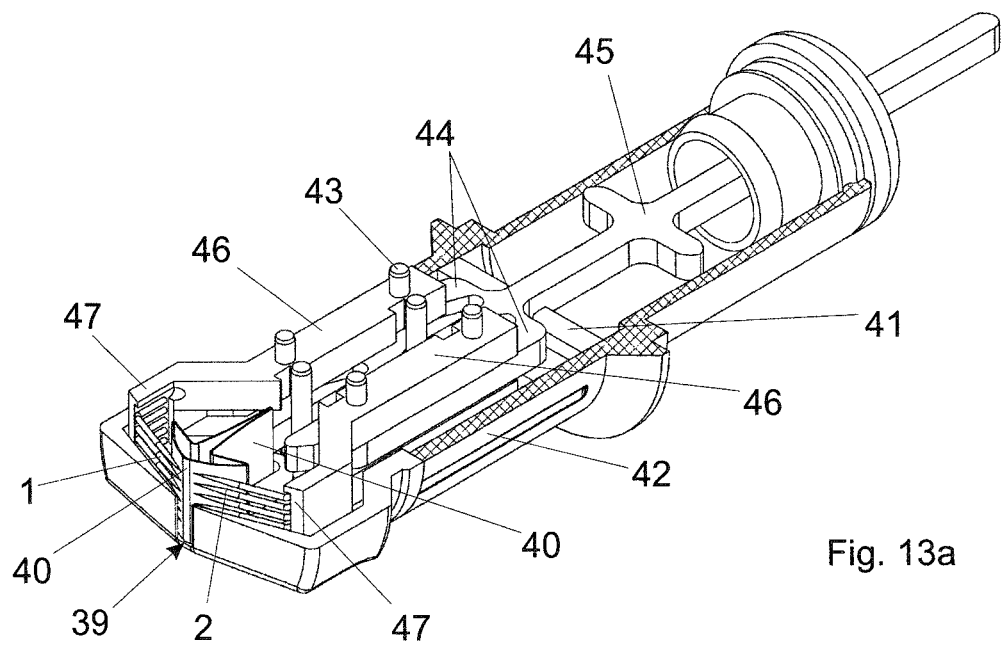
FIGS. 13a-13d show another form of embodiment of a mechanically operated device with the application tools in a position before piercing (initial position) and after piercing (penetration position)
Figure 13B:
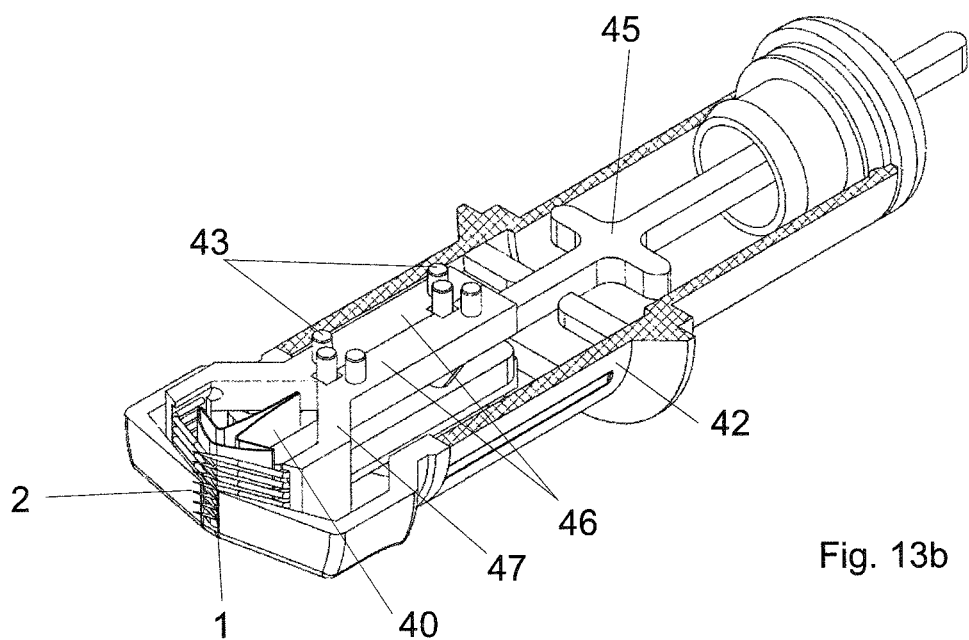

As shown in FIGS. 13a and 13b, two operating arms 46 which interact via guide pins 43 with an actuation element 44 of a mechanically-actuated actuation plunger 45 are moveably borne in a housing 42. The application tools 1, 2—in this case in needle form and guided on a tool guiding element 40 which simultaneously acts as a tissue penetration block—are formed on a tool holder 47 at the front ends of the operating arms 46. The application tools 1, 2 shown in an initial position before penetration in FIG. 13a, during the forward movement of the actuation plunger 45, and the thereby brought about displacement of the operating arms 46 in the opposite direction, are moved towards each other in order to pass through the opening 39 and be able to penetrated the tissue when the penetration device is placed on it, as shown in FIG. 13b.

Figure 13C:
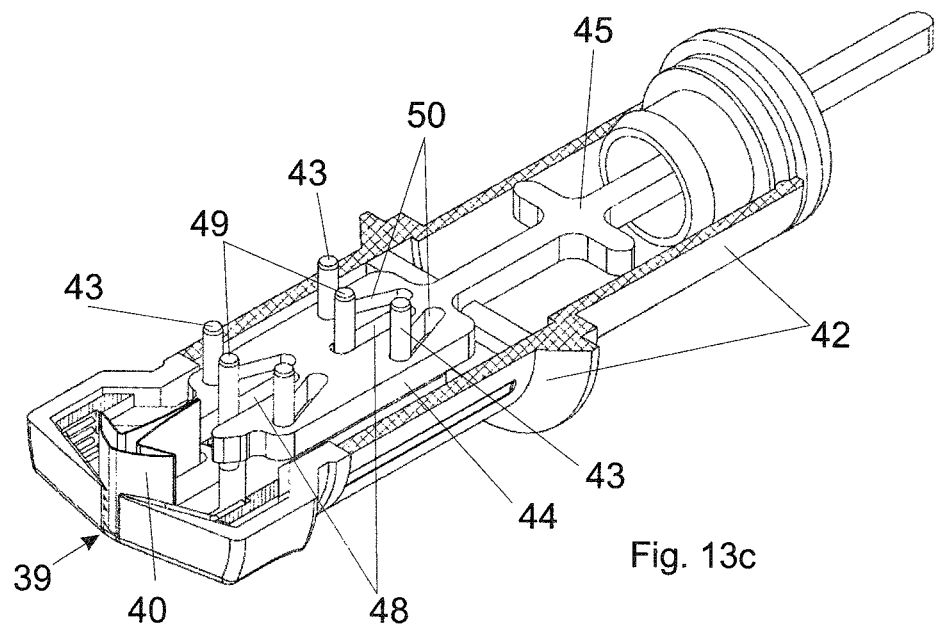
Figure 13D:
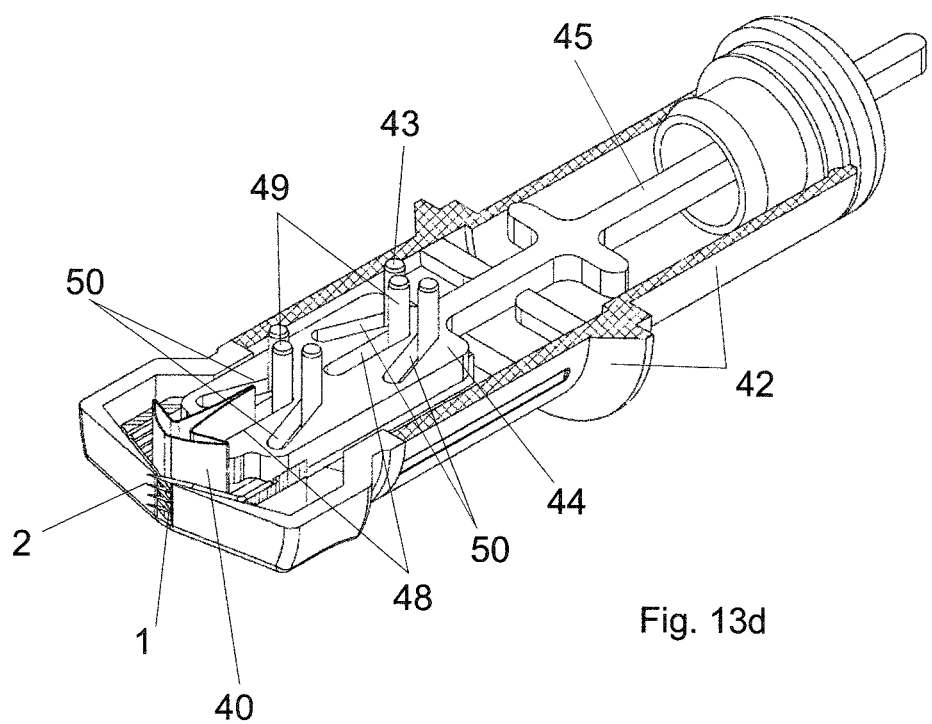

FIGS. 13c and 13d show the functioning of the actuation element 44 connected to the actuation plunger 45 for moving the operating arms 46 and thereby the application tools 1, 2. The actuation body 44 has first straight guide slits 48 which extend in the direction of the plunger movement and into which guide pins 49 attached to the housing 42 engage in order to linearly guide the actuation element 44. The guide pins 43, attached to the operating arms 46, also engage in second oblique guide slits 50 arranged in the actuating element 44, so that during the forward movement of the actuation plunger 45 the operating arms 46 are moved inwardly toward each other from the position shown in FIG. 13c into a position shown in FIG. 13c and so that the application tools 1, 2 can penetrate into the tissue through the opening 39 in a movement in which they cross each other. During the backwards movement of the actuation plunger 45, the operating arms 46 are pushed outwards again and the application tools 1, 2 are thereby retracted. A first retaining bar 41, formed on the actuation plunger 45, serves as a stop for a pressure spring (not shown) which is arranged between this and a further retaining bar formed on the housing and which moves the actuation plunger 45 into the initial position through spring force.

Figure 14:
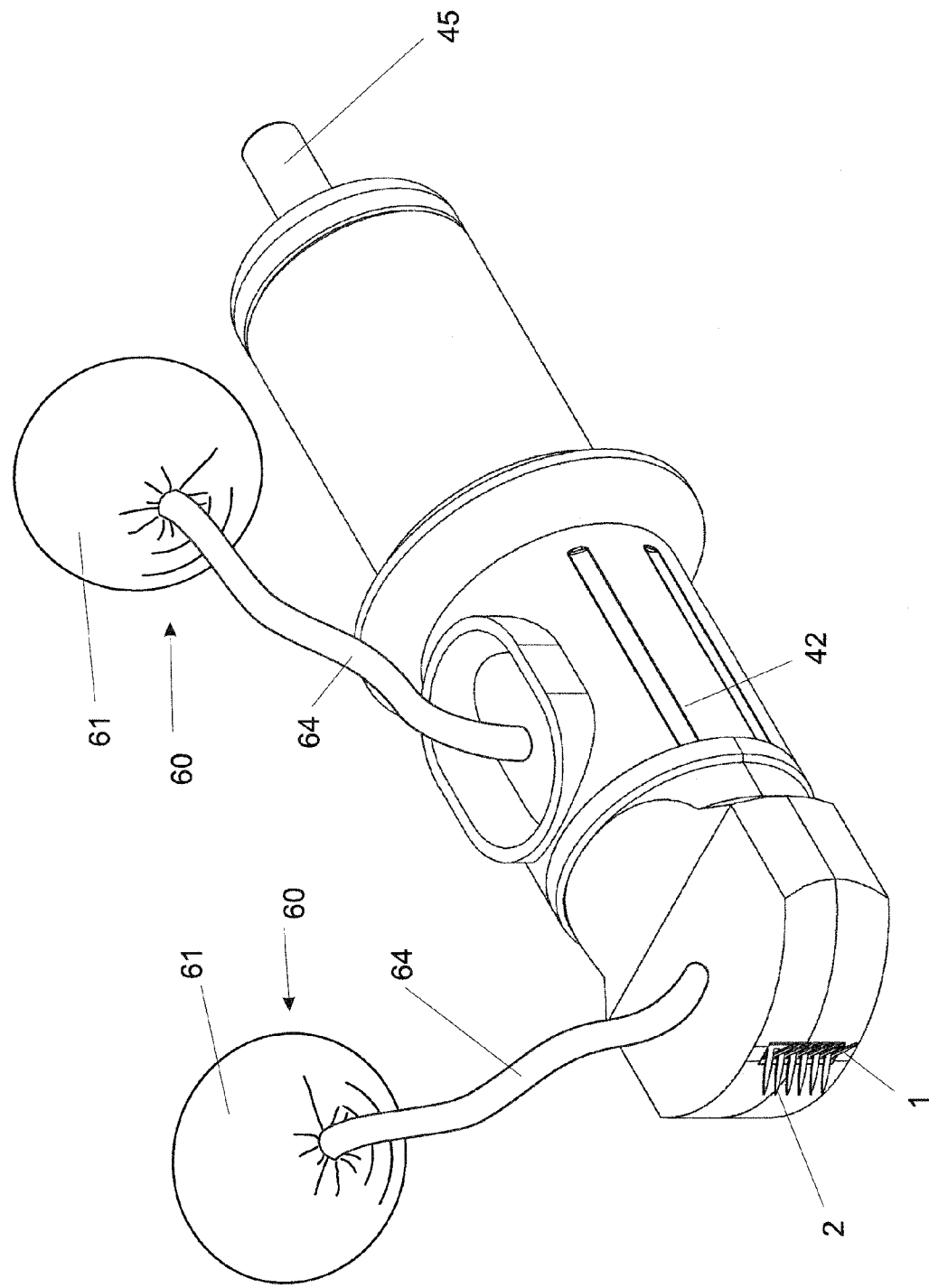
FIG. 14 shows an external view of a geometrical embodiment variant of a device for applying an active substance onto or into an organic tissue in accordance with FIGS. 12, 13 and 15 with a dispending device for the substance to be applied.

FIG. 14 shows a geometric embodiment variation of a housing 42 of a device for applying a substance from a schematically shown (double) dispensing device 60 onto or into an organic tissue in accordance with FIG. 12, 13 or 15 via the at least two application tools 1, 2 operated with an actuation plunger 45. In other embodiments, only one of the dispensing devices 60 shown in FIG. 14 is provided. Here, in the shown example, the storage container 61 is connected via a fluid pipeline 64 to the housing 42 in which the dispensed substance is then taken to the application tools 1, 2. The actuation plunger 45 can be connected, for example, to a commercially available motorized tattooing machine, so that the component shown in FIG. 14 acts as an interchangeable tattooing or piercing attachment (needle module). In this or in other embodiments the needle module with the application tools can be designed as a disposable article, which is discarded after use.

Figure 15A:
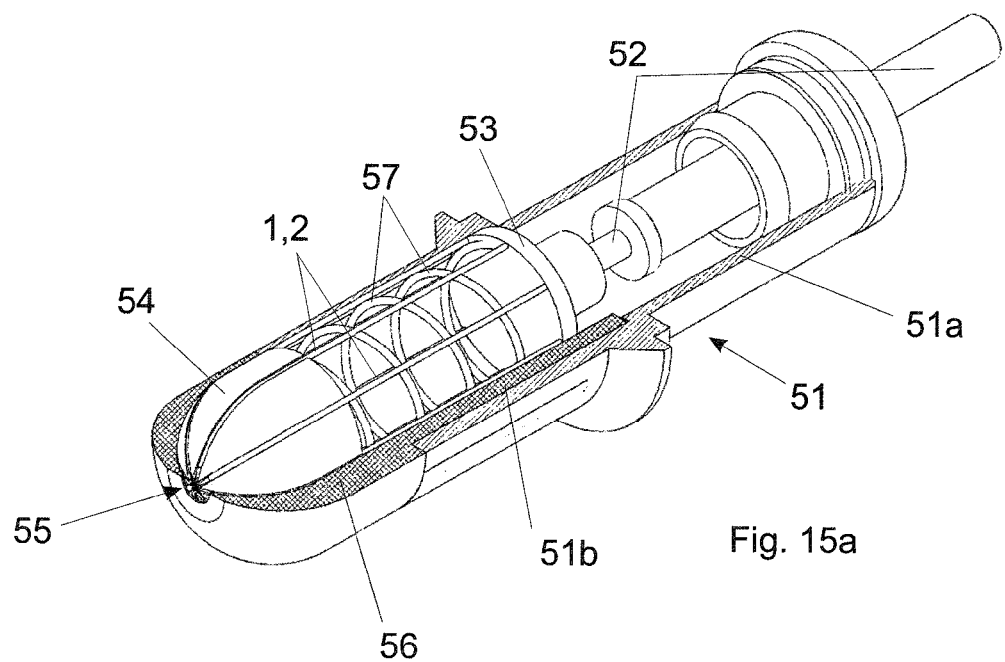
FIGS. 15a and 15b show a form of embodiment of a mechanically operated device with application tools arranged at an angle with regard to each other and acting on the tissue on an circular application line, in a position before piercing (FIG. 15a) and in position after piercing (FIG. 15b)
Figure 15B:
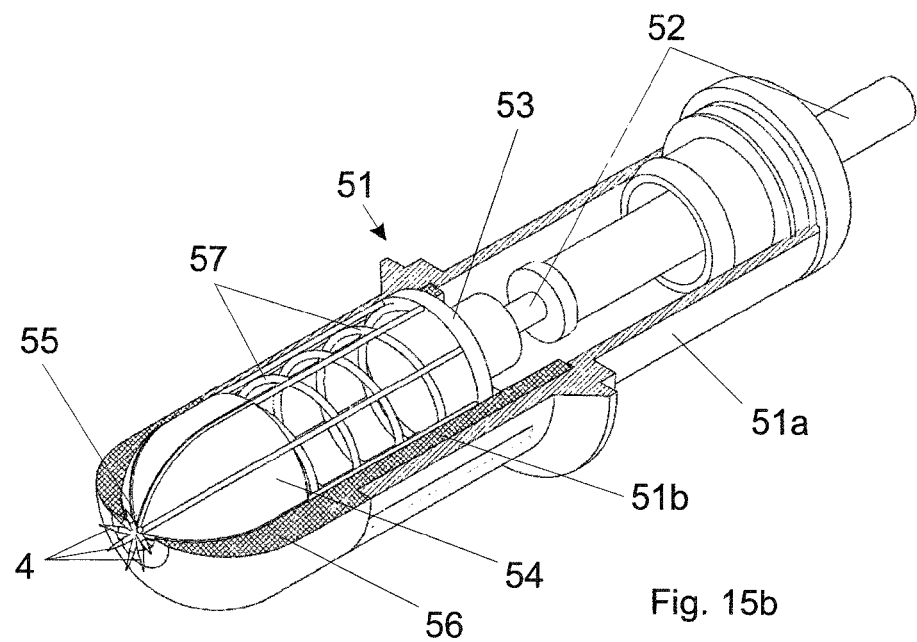

A further embodiment variant is shown in FIGS. 15a and 15b of a mechanically-actuated device that is in the form of a hand-held device. The device comprises an actuation plunger 52 which moves to-and-fro in a two-part housing 51 consisting of first and second housing section 51a, 51b, and which in an alternative embodiment can also be manually operated. Braced on a circular tool holder 53, on the actuation plunger 52 which is guided in housing section 51b, is a plurality of circularly arranged application tools 1, 2 which are guided (preferable in guiding grooves which are not shown here) between a rotationally symmetrical tool guiding element 54 with a convexly vaulted mantle surface and a correspondingly concavely vaulted outer tool guiding element 56 which opens into a circular opening 55. A pressure spring 57 is arranged between the tool holder 53 and the inner tool guiding element 54.

In the initial position shown in FIG. 15a, the tool tips 4 are positioned along a circular application line in the area of the round opening 55. During the forward movement of the actuation plunger 52 against the force of the pressure spring 57, the tool tips 4 of the application tools 1, 2 pass through the circular opening 55, whereby a majority of offset, circularly arranged, application tool pairs, which face each other and act in opposite directions to each other enclosing an angle $\alpha$, initially pretension and then penetrate the tissue. At the same time as or time-deferred with regard to the piecing of the tissue, a substance, for example a tattooing agent or another substance can be introduced into the tissue.

Figure 16:
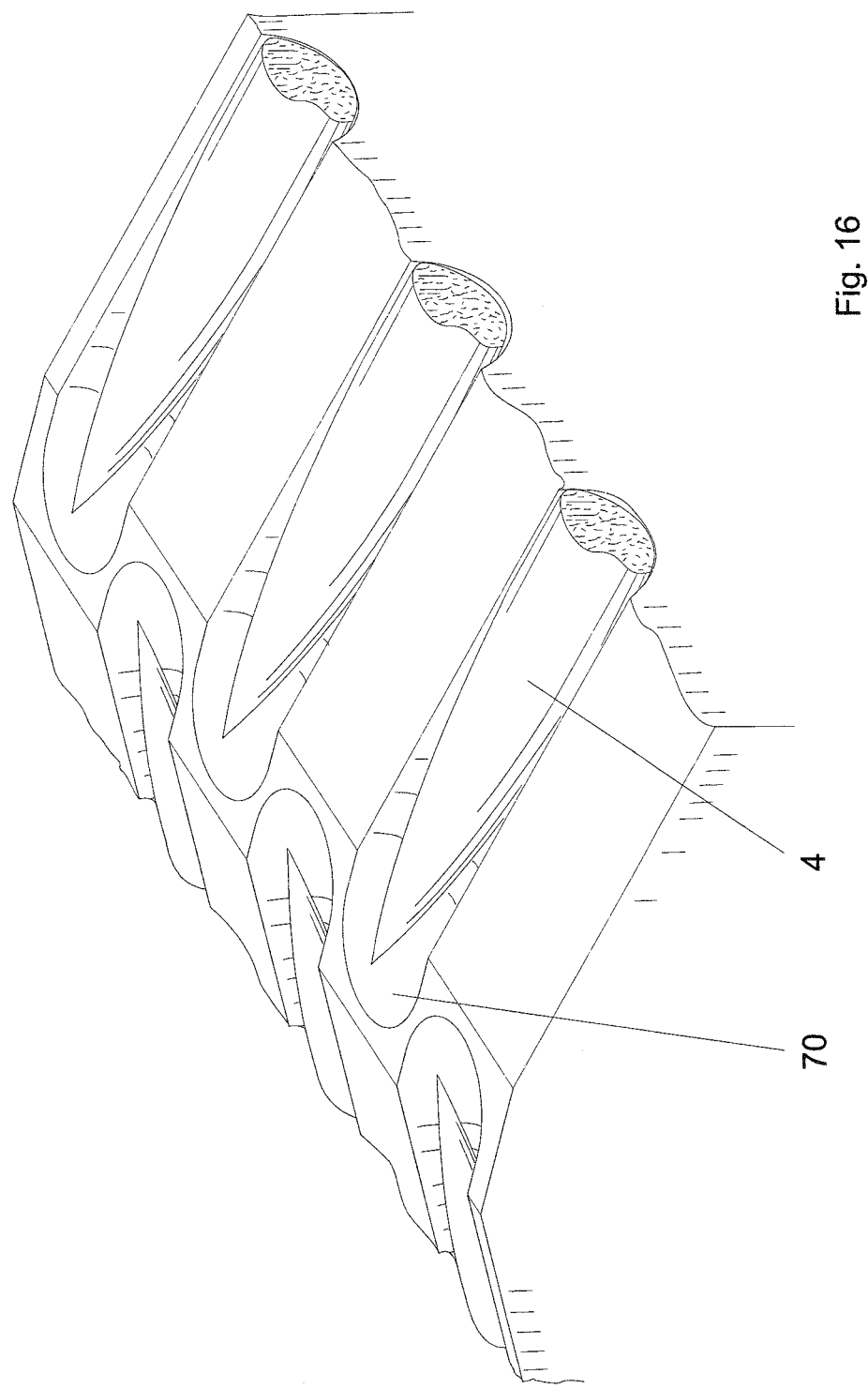
FIG. 16 shows a schematic view of the guiding of the distal tool ends in assigned holders.

FIG. 16 shows a schematic view of the mechanical guiding of the tool ends 4 of several application tools each in an assigned holder 70.

The features of the invention disclosed in the above description, the claims and the drawing can be of relevant both alone as well as in any combination for implementing the invention is its various forms of embodiment.

What is claimed is:
1. A device for the repeated piercing of an organic tissue with:
    a penetration device which has an operating mechanism and an arrangement of application tools each of which is connected to the operating mechanism and has a distal tool end which is formed for at least one application tool with a penetration element,
    the operating mechanism is configured to cause the application tools to displace relative to each other between an initial position and a penetration position, in that the at least one application tool and one other application tool of the arrangement are configured to be moved by the operating mechanism relative to each other, and
    in which, as the at least one application tool and one other application tool of the arrangement move relative to each other, the at least one application tool is arranged to provide an effect direction of an application force that is counter to an effect direction of the application force provided by the other application tool, and
    a mechanical actuation device which is connected to the operating mechanism and which is suitable for repeatedly effecting the relative displacement of the at least one application tool between the initial position and the penetration position with an operating frequency,
    wherein the application tool and the other application tool each are formed with a comb component on which several adjacent application elements are arranged transverse to a longitudinal extension of the device such that, in operation, all of the several adjacent application elements make contact with the organic tissue at the same time,
    wherein, a respective distal end of each application element is configured to cause a pre-tensioning of the organic tissue such that the other application tool supports the organic tissue as the at least one application tool pierces the organic tissue, and
    wherein the penetration device is arranged in a housing, wherein the application elements of the application tools extend at least partly through a slit opening which is formed in the housing such that, in operation, organic tissue is removed from the application elements by an edge of the slit opening when moving the application tools from the penetration position to the initial position.

2. The device according to claim 1, wherein with the device viewed in a direction perpendicular to the application force provided by the at least one application tool as well as by the other application tool, the at least one and the other application tool cross each other at least in the penetration position, such that an angle between the at least one application tool and the other application tool is larger than 0° and less than 180°.

3. The device according to claim 2, wherein during the relative movement towards the penetration position the at least one and the other application tool are guided laterally offset with regard to each other.

4. The device according to claim 2, wherein the application tools cross each other at least in the penetration position in the area of the distal tool ends themselves or in an area of projection lines of the distal tool ends.

5. The device according to claim 1, wherein during the relative movement towards the penetration position the at least one and the other application tool are guided laterally offset with regard to each other.

6. The device according to claim 1, wherein by means of the operating mechanism the relative movement between the initial position and the penetration position can be repeatedly carried out.

7. The device according to claim 1, wherein a movement path during the relative movement comprises at least one of a curved movement and a straight movement.

8. The device according to claim 1, wherein the penetration element of the at least one application tool is guided at least in a last section of the displacement movement to the penetration position along a direction of movement which assumes an angle, which differs from a right angle, with a contact surface assigned to the distal tool ends of the application tools during operation.

9. The device according to claim 1, wherein during the displacement movement between the initial position and the penetration position at least one of the at least one application tool and the other application tool are guided at least in sections in an assigned tool guide.

10. The device according to claim 1, wherein a path of the displacement movement of at least one of the at least one application tool and the other application tools can be adjusted.

11. The device according to claim 1, wherein in an area of at least one of the arrangement of the application tools and adjacent thereto, a tissue contact or tissue guide surface is formed.

12. The device according to claim 1, wherein the application elements of each application tool are formed on a common basic component.

13. The device according to claim 1, wherein the distal tool ends of the application tools are partially or fully retracted into the housing at least in the initial position.

14. The device according to claim 1, wherein a dispensing device is arranged on the penetration device and wherein the dispensing device is configured to dispense a substance to be applied.

15. The device of claim 1, wherein the actuating device is configured to generate an operating frequency of 20 Hz to 200 Hz.

16. A method for repeated piercing of an organic tissue with a device having a penetration device which has an operating mechanism and an arrangement of application tools each of which is connected to the operating mechanism and has a distal tool end which is formed for at least one application tool with a penetration element, said method comprises:
  displacement by way of the operating mechanism of the application tools relative to each other between an initial position and a penetration position repeatedly, in that the at least one application tool and one other application tool of the arrangement are moved relative to each other repeatedly; and
  countering an effect direction of an application force provided by the at least one application tool to an effect direction of the application force provided by the other application tool during the relative movement,
  wherein the application tool and the other application tool each are formed with a comb component on which several adjacent application elements are arranged transverse to a longitudinal extension of the device such that, in operation, all of the several adjacent application elements make contact with the organic tissue at the same time,
  wherein, during piercing of the organic tissue, the respective distal end of each application element causes a pre-tensioning of the organic tissue such that the piercing of the organic tissue by the at least one application tool is supported by the other application tool, and
  wherein the penetration device is arranged in a housing, wherein the application elements of the application tools extend at least partly through a slit opening which is formed in the housing such that, in operation, organic tissue is removed from the application elements by an edge of the slit opening when moving the application tools from the penetration position to the initial position.

17. A device for the repeated piercing of an organic tissue with:
  a penetration device which has an operating mechanism and an arrangement of application tools each of which is connected to the operating mechanism and has a distal tool end which is formed for at least one application tool with a penetration element,
  the operating mechanism is configured to cause the application tools to displaced relative to each other between an initial position and a penetration position repeatedly, in that the at least one application tool and one other application tool of the arrangement are configured to be move by the operating mechanism relative to each other repeatedly, and
  the at least one application tool is arranged to provide during the relative movement an effect direction of an application force that is counter to an effect direction of the application force provided by the other application tool, and
  a mechanical actuation device which is connected to the operating mechanism and which is suitable for repeatedly effecting the relative displacement of the at least one application tool between the initial position and the penetration position with an operating frequency,
  wherein with the device viewed in a direction perpendicular to the application force provided by the at least one application tool as well as by the other application tool, the at least one and the other application tool are arranged to cross each other at least in the penetration position, such that an angle between the at least one application tool and the other application tool is larger than 0° and less than 180°,
  wherein the application tool and the other application tool each are formed with a comb component on which several adjacent application elements are arranged transverse to a longitudinal extension of the device such that, in operation, all of the several adjacent application elements make contact with the organic tissue at the same time,
  wherein, in operation as the at least one application tool pierces the organic tissue, a respective distal end of each application element is configured to cause a pre-tensioning of the organic tissue such that the organic tissue is supported by the other application tool, and wherein the penetration device is arranged in a housing, wherein the application elements of the application tools extend at least partly through a slit opening which is formed in the housing such that, in operation, organic tissue is removed from the application elements by an edge of the slit opening when moving the application tools from the penetration position to the initial position.

\* \* \* \* \*

UNITED STATES PATENT AND TRADEMARK OFFICE
CERTIFICATE OF CORRECTION

PATENT NO. : 9,808,286 B2
APPLICATION NO. : 13/739086
DATED : November 7, 2017
INVENTOR(S) : Dirk Scherkowski Page 1 of 1

It is certified that error appears in the above-identified patent and that said Letters Patent is hereby corrected as shown below:

In the Claims

Column 20, Line 35, Claim 17:
"cation tools to displaced relative to each other between an"
Should read:
--cation tools to displace relative to each other between an--; and Column 20, Line 38, Claim 17:
"tool of the arrangement are configured to be move by the"
Should read:
--tool of the arrangement are configured to be moved by the--.

Signed and Sealed this
First Day of January, 2019

Andrei Iancu
*Director of the United States Patent and Trademark Office*